US009951349B2

(12) United States Patent
Rabinovich et al.

(10) Patent No.: US 9,951,349 B2
(45) Date of Patent: Apr. 24, 2018

(54) COMPOSITIONS AND METHODS FOR TRANSIENT EXPRESSION OF RECOMBINANT RNA

(71) Applicant: Yale University, New Haven, CT (US)

(72) Inventors: Peter M. Rabinovich, Madison, CT (US); Sherman M. Weissman, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/343,817

(22) PCT Filed: Sep. 27, 2012

(86) PCT No.: PCT/US2012/057617
§ 371 (c)(1),
(2) Date: Mar. 7, 2014

(87) PCT Pub. No.: WO2013/049389
PCT Pub. Date: Apr. 4, 2013

(65) Prior Publication Data

US 2014/0249212 A1 Sep. 4, 2014

Related U.S. Application Data

(60) Provisional application No. 61/539,713, filed on Sep. 27, 2011.

(51) Int. Cl.
*C12N 15/85* (2006.01)
*C12N 15/86* (2006.01)

(52) U.S. Cl.
CPC ............. *C12N 15/85* (2013.01); *C12N 15/86* (2013.01); *C12N 2760/18843* (2013.01); *C12N 2760/18852* (2013.01)

(58) Field of Classification Search
CPC ........... C12N 2760/18843; C12N 2760/20043; C12N 2760/18043; C12N 2760/14043; C12N 2760/16043; C12N 2501/603
See application file for complete search history.

(56) References Cited

U.S. PATENT DOCUMENTS 7,442,544 B2 * 10/2008 Nagai .................. C07K 14/005 424/211.1
7,569,127 B1 8/2009 Cho
2002/0090608 A1 7/2002 Palese
2002/0124896 A1 9/2002 OConnor
2003/0083305 A1 5/2003 Palese
2003/0109475 A1 6/2003 Debs
2004/0033235 A1 2/2004 Bolognesi
2004/0052820 A1 3/2004 Bolognesi
2005/0003343 A1 1/2005 Palese
2005/0256073 A1 11/2005 Lipford
2006/0110740 A1 5/2006 Hurwitz
2006/0216701 A1 9/2006 Palese
2007/0129305 A1 * 6/2007 Divita .................... C07K 14/00 514/130
2007/0280961 A1 * 12/2007 Billeter ................ A61K 39/165 424/212.1
2008/0260706 A1 10/2008 Rabinovich
2009/0028901 A1 1/2009 Palese
2009/0186337 A1 7/2009 Eleouet
2010/0196993 A1 8/2010 Nishimura
2010/0311171 A1 * 12/2010 Nakanishi ............ C12N 5/0696 435/456
2010/0323428 A1 * 12/2010 Yoshizaki ................ C12N 7/00 435/235.1
2011/0165133 A1 7/2011 Rabinovich
2011/0300164 A1 12/2011 Lipford
2012/0214240 A1 8/2012 Nakan1shi

FOREIGN PATENT DOCUMENTS

EP 1983048 10/2008
EP 2048232 4/2009
WO 200170400 9/2001
WO 2004034028 4/2004
WO WO 2008096811 A1 * 8/2008 ........... C07K 14/005
WO 2010134526 11/2010

OTHER PUBLICATIONS

Hasan et al. Creation of an infectious recombinant Sendai virus expressing the firefly luciferase gene from the 3' proximal first locus. Journal of General Virology, vol. 78, pp. 2813-2820, 1997.*
Grosfeld et al. RNA replication by repsiratory syncytial virus (RSV) is directed by the N, P, and L proteins: Transcription also occurs under these conditions but requires RSV superinfection for efficient synthesis of full-length mRNA. Journal of Virology, vol. 69, No. 9, pp. 5677-5686, Sep. 1995.*
Entry for “viral” in The American Heritage® Dictionary of the English Language, 5th edition Copyright© 2013 by Houghton Miffliin Harcourt Publishing Company. Accessed online at http://www.yourdictionary.com/viral on May 16, 2016 and printed as p. 1/1.*
Engelhorn et al. Molecular cloning and characterization of a Sendai virus internal deletion defective RNA. Journal of General Virology, vol. 74, pp. 137-141, 1993.*

(Continued)

*Primary Examiner* — Jennifer Dunston
(74) *Attorney, Agent, or Firm* — Pabst Patent Group LLP

(57) ABSTRACT

Compositions for transient but prolonged exogenous mRNA expression through the use of the transcription system of negative strand RNA viruses, and methods of use thereof are disclosed. In some embodiments, the system contains only RNAs and does not include any DNA molecules. The compositions typically include an RNA template unit (rTeUn) that includes a virus regulatory sequences operably linked to a coding sequence of interest. The rTeUn is typically transfected to a host cell's cytoplasm in the presence of virus expression system proteins that mediate replication of the rTeUn and transcription of the transgene. The rTeUn RNA bonded to viral proteins exhibits high resistance to degradation, prolonged duration of expression, and is free of viral genes. The compositions can be used to reprogram cell. For example, the compositions and methods can be used to redirected lymphocytes to target cancer cells, or to dedifferentiate somatic cells into induce pluripotent stem cells.

22 Claims, 4 Drawing Sheets

(56) References Cited

OTHER PUBLICATIONS

Salinas et al. Replication and Packaging properties of short Paramyxovirus defective RNAs. Virus Research. vol. 109, pp. 125-132, 2005.*

Wei et al. Comparison of the rescue efficiency of Sendai virus minigenome mediated by CMV and T7 promoter. Chinese Journal of Virology, vol. 28, No. 3, pp. 237-245, May 1, 2012, including a Google Translation of the reference printed as pp. 1/8-8/8, and a single page showing the date of publication.*

Peeples et al. Mutations in the 5' trailer region of a repsiratory syncytial virus minigenome which limit RNA replication to One Step. Journal of Virology, vol. 74, No. 1, pp. 146-155, Jan. 2000.*

Gonzalez et al. Selection of an optimal RNA transfection reagent and comparison to electroporation for the delivery of viral RNA. Journal of Virological Methods, vol. 145, pp. 14-21, 2007.*

Witko et al. An efficient helper-virus-free method for rescue of recombinant paramyxoviruses and rhadoviruses froom a cell line suitable for vaccine development. Journal of Virological Methods, vol. 135, pp. 91-101, 2006.*

Park et al. Rescue of a foreign gene by Sendai virus. Proceedings of the National Academy of Sciences, USA, vol. 88, pp. 5537-5541, Jul. 1991.*

Kato et al. Initiation of Sendai virus multiplication from transfected cDNA or RNA with negative or positive sense. Genes to Cells, vol. 1, pp. 569-579, 1996.*

Boyce et al. Development of reverse genetics systems for bluetongue virus: Recovery of infectious virus from synthetic RNA transcripts. vol. 82, No. 17, pp. 8339-8348, Sep. 2008.*

MMESSAGE mMACHINE® Kit (Cat #AM1340, AM1344, AM1348) Instruction Manual, Manual 1340M Revision B, pp. 1-32, Ambion, Inc., Jan. 4, 2007.*

Bitzer, et al., "Sendai virus vectors as an emerging negative-strand RNA viral vector system" J Gene Med., 5 (7):543-53(2003).

Collins, et al., "Viral vectors in cancer immunotherapy: which vector for which strategy", Curr Gene Ther., 8 (2):66-78 (2008).

EMBL Sequence No. X17008.1, "Sendai virus polymerase (P) gene (strain fushimi)", 4 pages, first appeared Dec. 12, 1989, last updated Apr. 18, 2005, accessed Jun. 12, 2014.

EMBL Sequence No. X17218.1, "Sendai virus strain Fushimi genomic RNA for nucleocapsid protein (NP)", 3 pages, first appeared May 11, 1993, last updated May 11, 1993, accessed Jun. 12, 2014.

Fusaki, et al., "Efficient induction of transgene-free human pluripotent stem cells using a vector based on sendai virus, an RNA virus that does not integrate into the host genome", Proc. Jpn Acad Ser., 85:348-308 (2009).

Garci•A-Sastre, "Negative-strand RNA viruses: applications to biotechnology", Trends Biotechnol., 16(5):230-5 (1998).

Genbank Accession No. AB039658.1, "Sendai virus genomic RNA, complete genome", 8 pages, first appeared Dec. 28, 2000, last updated Sep. 15, 2007, accessed Jun. 9, 2014.

Genbank Accession No. AB065186.1, "Sendai virus genomic RNA, complete genome, clone:E30cl2, viral complementary sequence"; 8 pages, first appeared Jul. 9, 2003, last updated Jun. 20, 2008, accessed Jun. 9, 2014.

Genbank Accession No. A8065187.1; Sendai virus genomic RNA, complete genome, clone:E15cl2, viral complementary sequence, 8 pages, first appeared Aug. 12, 2002, last updated Jun. 20, 2008, accessed Jun. 9, 2014.

Genbank Accession No. AB065189.1; Sendai virus genomic RNA, complete genome, clone:E30M15cl5, viral complementary sequence, 8 pages, first appeared Jul. 9, 2013, last updated Jun. 20, 2008, accessed Jun. 9, 2014.

Genbank Accession No. AB195967.1, "Sendai virus genomic RNA, complete genome, strain:pi", 7 pages, first appeared Dec. 4, 2004, last updated Jun. 20, 2008, accessed Jun. 9, 2014.

Genbank Accession No. AB195968.1, "Sendai virus genomic RNA, complete genome, strain:Nagoya", 7 pages, first appeared Dec. 4, 2004, last updated Jun. 20, 2008, accessed Jun. 9, 2014.

Genbank Accession No. AB275417.1, "Sendai virus genomic RNA, complete genome, strain: Nagoya 1-60", 6 pages, first appeared Jul. 16, 2007, last updated Sep. 12, 2007, accessed Jun. 9, 2014.

Genbank Accession No. EF679198.1, "Sendai virus strain Tianjin, complete genome", 7 pages, first appeared Jul. 16, 2007, last updated Sep. 12, 2007, accessed Jun. 9, 2014.

Grudzien-Nogalska, et al., "Phosphorothioate cap analogs stabilize mRNA and increase translational efficiency in mammalian cells", RNA 13 (10):1745-1755 (2007).

Hacein-Bey-Abina, et al., "LMO2-associated clonal T cell proliferation in two patients after gene therapy for SCID-X1", Science, 302 (5644):415-9 (2003).

Holtkamp, et al., "Modification of antigen-encoding RNA increases stability, translational efficacy, and T-cell stimulatory capacity of dendritic cells", Blood, 108 (13):4009-17 (2006).

Kay, "State-of-the-art gene-based therapies: the road ahead", Nat Rev Genet., 12 (5):316-28 (2011).

Lewitzky and Yamanaka, "Reprogramming somatic cells towards pluripotency by defined factors", Curr. Opin Biotech., 18:467-73 (2007).

NCBI Reference Sequence: NC_001552.1, "Sendai virus strain, complete genome", 9 pages, first appeared Aug. 1, 2000, last updated Aug. 23, 2012, accessed Jun. 9, 2014.

Nishimura, et al., "Development of defective and persistent sendai virus vector; a unique gene delivery/expression system ideal for cell reprograming", J Biological Chem., 286(6):4760-71 (2011).

Okita, et al., "Induction of pluripotency by defined factors", Exp Cell Res., 316(16):2565-70 (2010).

Porter, et al., " Chimeric antigen receptor-modified T cells in chronic lymphoid leukemia", N Eng J Med., 365 (8):725-33 (2011).

Rabinovich, et al., "Cell engeenering with synthetic messenger RNA", Methods Mol Biol., 969:3-28 (2013).

Rabinovich, et al., "Synthetic messenger RNA as a tool for gene therapy", Hum. Gene Ther., 17(10):1027-35 (2006).

Rabinovich, et al., "Chimeric receptor mRNA transfection as a tool to generate antineoplastic Lymphocytes", Hum Gene Ther., 20(1):51-61 (2009).

Ritter, et al., "Gene therapy in transplantation: Toward clinical trials", Curr Opin Mol Ther., 11 (5):504-12 (2009).

UniProtKB/Swiss-Prot P12575, (FUS_SENDF), 6 pages, first appeared Oct. 1, 1989, last updated Feb. 19, 2014, accessed Jun. 9, 2014.

UniProtKB/Swiss-Prot P19758 (HN_Sendf), 6 pages, first appeared Feb. 1, 1991, last updated Apr. 16, 2014, accessed Jun. 12, 2014.

UniProtKB/Swiss-Prot Q06996 (L_SENDF), pages, first appeared Oct. 1, 1996, updated Apr. 16, 2014, accessed Jun. 12, 2014.

Walpita, et al., "Reverse genetics of negative-stranded RNA viruses: a global perspective", FEMS Microbiol Lett, 244 (1):9-18 (2005).

Warren, et al., "Highly efficient reprogramming to pluripotency and directed differentiation of human cells with synthetic modified mRNA", Cell Stem Cell, 7(5):618-30 (2010).

Yamamoto, et al., "Current prospects for mRNA gene delivery", Eur J Pharm Biopharm., 71(3):484-9 (2009).

Yoshizaki, et al., "Naked Sendai virus vector lacking all of the envelope-related genes: reduced cytopathogenicity and immunogenicity", J. Gene Med., 8(9):1151-9 (2006).

Nakanish and Otsu, " Development of sendai virus vectors and their potential applications in gene therapy and regenerative medicine", Curr Gene Ther., 12(5):410-6 (2012).

Stepinski, et al., "Synthesis and properties of mRNAs containing the novel "anti-reverse" cap analogs 7-methyl(3'-O-methyl)GpppG and 7-methyl (3'-deoxy)GpppG", RNA, 7(10):1486-95 (2001).

* cited by examiner

2A

2B

COMPOSITIONS AND METHODS FOR TRANSIENT EXPRESSION OF RECOMBINANT RNA

CROSS-REFERENCE TO RELATED APPLICATIONS

This application is a 371 application of International Application No. PCT/US2012/057617, filed Sep. 27, 2012, which claims the benefit of and priority to U.S. Provisional Application No. 61/539,713, entitled "Prolonged recombinant protein expression via mRNA stabilization" filed Sep. 27, 2011.

STATEMENT REGARDING FEDERALLY SPONSORED RESEARCH OR DEVELOPMENT

This invention was made with government support under Agreement NIH P50 HG002357 awarded by the National Institutes of Health. The government has certain rights in the invention.

REFERENCE TO SEQUENCE LISTING

The Sequence Listing submitted May 20, 2014 as a text filed named "YU_5287_ST25.txt," created on May 20, 2014 and having a size of 52,903 bytes is hereby incorporated by reference.

FIELD OF THE INVENTION

The invention is generally drawn to compositions and method for stabilization and prolonged expression of RNA transiently transfected into cells.

BACKGROUND OF THE INVENTION

The use of viral vectors for cell reprogramming is a powerful approach for translational medicine. Promising results have been obtained with the use of viral transduction in stem cell research (Okita, et al., (2010) Exp Cell Res 316 (16):2565-2570. doi:10.1016/j.yexcr.2010.04.023), transplantation (Ritter, et al., (2009) Curr Opin Mol Ther 11 (5):504-512), and immunotherapy (Collins, et al., (2008) Curr Gene Ther 8 (2):66-78). Recent clinical trial results using this approach to reprogram T cells against lymphomas are encouraging (Kay (2011) Nature Reviews Genetics 12 (5):316-328). Still, the introduction of viral genomes into human cells leads to some negative consequences, among them: (a) genomic integration of the viral vectors, leading to insertional mutagenesis, and potential transformation of the host cells (Hacein-Bey-Abina, et al., (2003) Science (New York, N.Y.) 302 (5644):415-419); (b) long or permanent presence of reprogrammed cells in the body that increase the burden on immune system and can lead to distant complications after completion of the treatment (Porter, et al., (2011) New England Journal Medicine 365 (8):725-733); (c) continuing production of viral proteins that could induce host immune responses.

The use of non-integrated viral vectors can reduce the risk of insertional mutagenesis; but this does not address the problem of long-term persistence of vector and raises concerns of uncontrolled viral modification in host cells.

Transfection with synthetic mRNA is an important method of cell reprogramming that makes it possible to avoid the abovementioned problems (Rabinovich et al., 2009, Rabinovich P M, Weissman S M (2012) Cell engineering with synthetic messenger RNA Synthetic Messenger RNA and Metabolism Modulation Methods in Molecular Biology 969 (In Press)). mRNA introduced into cells exists only in the cytoplasm and does not cause genome perturbations. mRNA mediated reprogramming is essentially transient. Unless expression of the mRNA changes the cell epigenetically, transient transfection is limited by the time of mRNA and cognate protein persistence in the cell, and does not continue after degradation of cognate proteins.

Despite its attractive features, present technologies for mRNA transfection are hampered by the relatively rapid degradation of mRNA. In general, mRNA half-life is short and often is in the range of 2-5 h. Short mRNA persistence makes the duration of its expression mainly a function of the cognate protein stability. For example, the duration of expression of stable proteins can last weeks. Alternatively, the unstable protein HOXB4 can be detected for only a few hours after transfection of its encoding mRNA. Similarly, secretory proteins, excreted from cells soon after translation from transfected mRNA, are generally detected in the cells only for a few hours after transfection. Some methods have been employed to increase mRNA stability, for example, protection of mRNA termini from exonuclease degradation (Holtkamp, et al., (2006). Modification of antigen-encoding RNA increases stability, translational efficacy, and T-cell stimulatory capacity of dendritic cells. Blood 108 (13):4009-4017) (Grudzien-Nogalska, et al., (2007) RNA 13 (10): 1745-1755) (Rabinovich, et al., (2006) Hum Gene Ther 17 (10):1027-1035), however these methods alone are generally insufficient to substantially increase the duration of expression of cognate proteins in cells.

Another approach to cell reprogramming includes the use of negative strand RNA viruses that can form highly stable cytoplasmic ribonucleoprotein structures with a long lasting ability for mRNA and protein synthesis (Biology of Negative Strand RNA Viruses: The Power of Reverse Genetics (2010)). However, the use of viral RNA to produce viral vectors is hampered by the inability of the naked viral RNA to efficiently initiate viral transcription or replication. Attempts to address this problem include the use various DNAs encoding viral vector, viral nucleocapsid protein (NP) and the replicase/transcriptase complex proteins P and L to rescue the viral genome RNA. NP encapsidates viral RNA in a nucleoprotein complex, and makes the RNA highly resistant to nuclease degradation; and P and L form PL, a complex that recognizes NP-encapsidated viral RNA and carries out at least two enzymatic activities: NP-RNA dependent RNA polymerase and NP-RNA dependent transcriptase (Walpita, et al., (2005). FEMS Microbiol Lett 244 (1):9-18); (Bitzer, et al., (2003) J Gene Med 5 (7):543-553).

The standard Sendai vector rescue system includes a plasmid coding viral RNA expression cassette under a T7 promoter, and 3 supplemental plasmids coding NP, P and L protein, also under T7 promoters. These four plasmids can be introduced in cells to produce T7 polymerase to produce viral vector RNA and NP, P and L proteins (Bitzer, et al., (2003) J Gene Med 5 (7):543-553). The rescue occurs with very low efficiency, usually $<10^{-6}$, however, following rescue, the viral vector can replicate and produce viral particles sufficient for further rounds of transduction. In an alternative design, the rescue can be provided in cells which contain viral packaging proteins, namely F, M and NH (Yoshizaki, et al., (2006) J Gene Med 8 (9):1151-1159). In this case viral particles would contain defective virus, not able to produce complete viral particles outside of the packaging cells. In both cases, targeted cells obtained virus that continued to produce viral proteins such as N, P, and L and was able to replicate itself or, potentially, even to recover some level of virulency as result of natural propagation and selection.

Accordingly, it is an object of this invention to provide compositions and methods for cell reprogramming with improved safety and efficacy.

It is also an object of the invention to provide compositions and methods for prolonged recombinant protein stability and expression in cells via transient transfection of mRNA.

SUMMARY OF THE INVENTION

Compositions for transient but prolonged exogenous mRNA expression through the use of a transcription system of negative strand RNA viruses, and methods of use thereof are disclosed. In some embodiments, the system contains only RNAs as coding molecules and does not include any DNA molecules. The compositions typically include a recombinant RNA, template unit (rTeUn), able to be replicated and transcribe in a host cell's cytoplasm. The rTeUn RNA construct, bounded to specific proteins, exhibits high resistance to degradation, prolonged duration of expression, and is free of viral genes.

The template contains regulatory sequences from a negative strand RNA virus, for example, Sendai virus, which flank sequences encoding a transgene of interest. The rTeUn does not contain any intact, viral genes. When transfected into a host cells in the presence of viral transcriptional proteins, the rTeUn can be replicated and transcribed in the host cell. In some embodiments, the rTeUn includes regulatory sequences from Sendai virus and is transfected into cells in the presence of the Sendai virus proteins NP, P and L. The NP protein binds to and stabilizes rTeUn while the P and L proteins, which form the viral replicase/transcriptase complex, bind to the rTeUn-NP complex and induce transcription of rTeUn transgene. The NP, P, and L proteins can be introduced into the cell as proteins, as one or more exogenous mRNA encoding the NP, P, and L proteins. In a preferred embodiment, exogenous mRNA encoding the NP, P, and L proteins are introduced into the host cells and translated into protein by the host cells' translation system.

After degradation of any of the NP, P, and L exogenous mRNAs and proteins, the rTeUn RNA complex loses the ability to replicate or to be transcribed. However, the rTeUn construct, being complexed with specific proteins, is more stable in the cytosol than conventional mRNA, therefore, the rTeUn remains in the cytosol longer than transiently delivered mRNA or protein. This mechanism can be used to control the duration of expression. For example, reintroduction of additional viral NP, P, and L mRNAs or proteins can reactivate replication and transcription of the rTeUn and prolong expression of the transgene. The Examples below show that the synthetic rTeUn RNA construct can express cognate protein in the cell cytoplasm for as long as two weeks without reactivation, and over a month when reactivated. Without reactivation the NP.L and P proteins eventually disappear and the rTeUn construct is degraded by the host cell's RNA degradation machinery. This ensures that presence and expression of rTeUn in cells can be strictly limited.

The rTeUn transgene can encode a polypeptide of interest and/or non-translated functional nucleic acid, such as long non-coding RNA and other regulatory RNA (obtained directly from rTeUn or as result of degradation of rTeUn transcripts), including miRNAs, siRNAs, and ribozymes and external guide sequences, If the transgene encodes a polypeptide, transcription of the rTeUn results in mRNA that can be recognized and translated by the host cell's translation system. Accordingly, the prolonged presence of the rTeUn in the cytosol of the cell increases the duration of protein expression of template RNA compared to convention exogenous mRNA.

In some embodiments, the rTeUn is packaged into virus-like particles by viral packaging proteins such as F, RN, and M proteins from Sendai virus. The virus-like particles can be used to enhance delivery of the rTeUn to a cell.

Methods of using the compositions to reprogram cells are also disclosed. The methods can be used to deliver tTeUn encoding mRNAs or other non-translated functional RNAs into cells in vitro and in vivo, and modulate cell activity. The methods can be used to de-differentiate, re-differentiate, or re-program cells. In some embodiments, the compositions are used for immunomodulation or de-differentiation. For example, cells can be induced to form induced pluripotent stem (iPS) cells. Cells prepared according to the methods are useful in research and cell therapy, for example, by administering the cells to a subject in need thereof for the treatment or alleviation of one or more symptoms of a disease or disorder. The compositions and methods makes it possible to reprogram almost the entire cell population with one or multiple transgenes, to increase the time of mRNA accessibility for translation, and to increase the overall duration of mRNA retention.

BRIEF DESCRIPTION OF THE DRAWINGS

FIGS. 5A, B; not treated cells.

DETAILED DESCRIPTION OF THE INVENTION

I. Definitions

Figure 1:
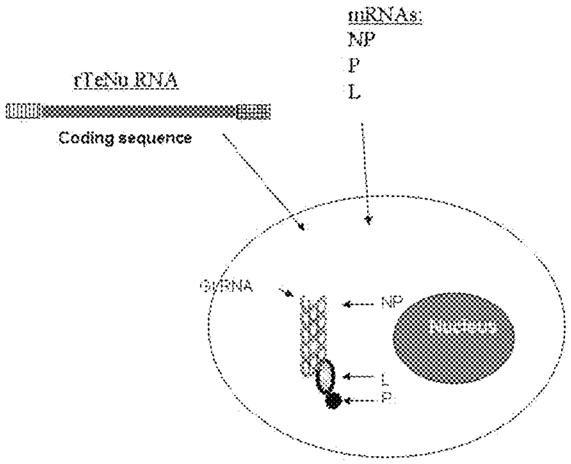
FIG. 1 is a schematic representation of GFP rTeUn rescue with supplemental mRNAs.

The brief life of an mRNA molecule begins with transcription and ultimately ends in degradation. During its life, an mRNA molecule may be processed, edited, and exported to the cytoplasm. During transcription, RNA polymerase makes a copy of a gene from the DNA or RNA template to make mRNA as needed. Eukaryotic RNA polymerase associates with mRNA processing enzymes during transcription so that processing can proceed quickly after the start of transcription. The short-lived, unprocessed or partially processed, product is termed pre-mRNA; once completely processed, it is termed mature mRNA.

As used herein, a 5' cap (also termed an RNA cap) is a modified guanine nucleotide that has been added to the "front" or 5' end of an eukaryotic messenger RNA shortly after the start of transcription. The 5' cap consists of a terminal group which through a triphosphate bridge is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

Eukaryotic mRNA that has been processed and transported to the cytoplasm (i.e. mature mRNA) can then be translated by the ribosome. Translation may occur at ribosomes free-floating in the cytoplasm, or directed to the endoplasmic reticulum. After a certain amount of time, the message is degraded by RNases into its component nucleotides. The limited longevity of mRNA enables a cell to alter protein synthesis rapidly in response to its changing needs.

Different mRNAs within the same cell have distinct lifetimes. In bacterial cells, individual mRNAs can survive from seconds to more than an hour; in mammalian cells, mRNA lifetimes range from several minutes to days. The greater the stability of an mRNA, the more protein may be produced from that transcript. The presence of AU-rich motifs in some mammalian mRNAs tends to destabilize those transcripts through the action of cellular proteins that bind these motifs. Rapid mRNA degradation via AU-rich motifs is a critical mechanism for preventing the overproduction of potent cytokines such as tumor necrosis factor (TNF) and granulocyte-macrophage colony stimulating factor (GM-CSF). Base pairing with a small interfering RNA (siRNA) or microRNA (miRNA) can also accelerate mRNA degradation.

As used herein, "transient" refers to expression of a non-integrated transgene for a period of time which is less than the period of time for expression of the gene if integrated into the genome or contained within a stable plasmid replicon in the host cell.

As used herein, a "promoter site" is a sequence of nucleotides to which an RNA polymerase, such as the DNA-dependent RNA polymerase originally isolated from bacteriophage, described by Davanloo, et al., *Proc. Natl. Acad. Sci. USA,* 81:2035-39 (1984), or from another source, binds and initiates transcription, as described by Chamberlin, et al., *Nature,* 228:227-231 (1970).

As used herein, a "poly(A)" is a series of adenosines attached to the 3' end of mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as mRNA stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

As used herein "translation system" refers to the components necessary to incorporate amino acid into a growing polypeptide chain (protein). Components of a translation system can include, e.g., ribosomes, tRNAs, synthetases, mRNA and the like. The components described herein can be added to a translation system, in vivo or in vitro. A translation system can be either prokaryotic, e.g., an *E. coli* cell, or eukaryotic, e.g., a yeast, mammal, plant, or insect or cells thereof.

As used herein, "viral transcriptional system" "viral transcriptional system protein(s)" and "virus transcription protein(s)" and used interchangeably and refer to viral proteins that are necessary for transcription of genes in the viral genome. The viral transcription proteins induce transcription, for example, by first recognizing and binding to one or more regulatory sequences, referred to herein as "viral regulatory sequence(s)," which are present in the viral genome. This includes, but is not limited to protein recognition elements in general, promotors and terminators of transcription or replication, leader and trailer sequences. As discussed in more detail below, viral regulatory sequences can be operably-linked to any heterologous RNA coding sequence of interest in such a way that the obtained RNA construct can be recognized and transcribed or replicated by viral protein(s). An example of viral transcriptional and replication proteins are the NP, P, and L proteins from Sendai virus.

As used herein, "viral packaging system," "viral packaging system protein(s)" and "virus packaging protein(s)" are used interchangeably and refer to the viral proteins that are necessary for forming virus like particles. The proteins typically include structural proteins, such as Envelope or Capsid, which self-assemble into virus like particles in the absence of a complete viral genome. An example of viral packaging system proteins are the HN, M, and F proteins from Sendai virus.

As used herein, "virus like particles" or "VLP" means a biological construct designed to look like a virus, but which does not contain a complete viral genome. VLPs are assembled from viral proteins. Virus like particles can be loaded with heterologous constructs such as rTeUn.

As used herein, "RNA template unit" or "rTeUn" refers to a RNA construct which includes viral regulatory sequences operably linked to a coding sequence of interest, such that that the coding sequence can be expressed by the components of viral expression system. For example, if the rTeUn encodes a polypeptide, viral protein mediated transcription of the TeUn results in mRNA that can be translated by a host cell's translation system.

As used herein in a more general sense, rTeUn refers to a recombinant nucleic acid sequence encoding not only mRNA, but also non-translated functional RNAs. Non-translated functional RNA may include long non-coding RNA and other regulatory RNA (obtained directly from rTeUn or as result of degradation of rTeUn transcripts), including miRNAs, siRNAs, ribozymes and external guide sequences.

The term "construct" refers to a recombinant genetic molecule having one or more isolated polynucleotide sequences.

The term "regulatory sequence" refers to a nucleic acid sequence that controls and regulates the function, for example, transcription and/or translation of another nucleic acid sequence. Control sequences that are suitable for prokaryotes, may include a promoter, optionally an operator sequence and/or a ribosome binding site. Eukaryotic cells are known to utilize sequences such as promoters, terminators, polyadenylation signals, and enhancers. Regulatory sequences include viral protein recognition elements that control transcription and replication of viral genes.

As used herein "to reprogram a cell" or "cellular reprogramming" means to induce a cell to express one or more functional nucleic acids in an effective amount to change a function of the cell. The function can be any function. For example, an immune cell can be induced to express a receptor which changes the cell's ability to recognize an antigen and/or to mediate an immune response; or a somatic cell can be induced to dedifferentiate from a somatic state to a pluripotent state (i.e., induced pluripotent stem cell (iPS)).

"Operably linked" refers to a juxtaposition wherein the components are configured so as to perform their usual function together. For example, regulatory sequences operably linked to a coding sequence are capable of effecting the expression of the coding sequence. In another example an organelle localization aminoacid sequence operably linked to protein will assist the linked protein in being localized at the specific organelle.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, *flagellates*, microsporidia, and protists.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory sequences and can include 5' and 3' ends.

The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Be, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides which do not significantly alter the characteristics of the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3);

proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±I are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within +1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences."

"Transfected" or "transduced" refers to a host cell or organism into which a heterologous nucleic acid molecule has been introduced. The nucleic acid molecule can be stably integrated into the genome of the host or the nucleic acid molecule can also be present as a stable or unstable extrachromosomal structure. Such an extrachromosomal structure can be auto-replicating. Transformed cells or organisms may to encompass not only the end product of a transformation process, but also transgenic progeny thereof. A "non-transformed," or "non-transduced" host refers to a cell or organism, which does not contain the heterologous nucleic acid molecule.

The term "endogenous" with regard to a nucleic acid refers to nucleic acids normally present in the host.

The term "heterologous" refers to elements occurring where they are not normally found. For example, an endogenous promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

As used herein, the term "purified" and like terms relate to the isolation of a molecule or compound in a form that is substantially free (at least 60% free, preferably 75% free, and most preferably 90% or more free) from other components normally associated with the molecule or compound in a native environment.

"Protein Transduction Domain" or PTD refers to a polypeptide, polynucleotide, carbohydrate, or organic or inorganic compounds that facilitate traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs can include, for example, 11 Arginine residues, or positively charged polypeptides or polynucleotides having 8-15 residues, preferably 9-11 residues.

Unless otherwise indicated, the disclosure encompasses conventional techniques of molecular biology, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(F. M. Ausubel, et al. eds., (1987)]; Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

II. Compositions for Transient Transfection of RNA Transgenes

The compositions disclosed herein allow for RNA-mediated cell transfection with one or more RNA transgenes. In some embodiments, the transfection is DNA-free. The compositions enable prolonged lifetime and expression of the rTeUn RNA in a transfected cell's cytoplasm compared to conventionally prepared and transfected exogenous mRNA. The compositions rely on the use of proteins from a negative strand virus, but can be used without live virus, or even viral genes which could replicate, or recover virulence as a result of natural propagation and selection. As described in more detail below, in some embodiments the compositions are used in methods of cell reprogramming.

The compositions and methods offer a number of advantages over conventional cell reprogramming technologies. The compositions and methods are safer than methods based DNA-based transgene expression and reprogramming methodology because (1) although persistence of the RNA transgene in the cell is prolonged, it is not permanent; and (2) the compositions are unlikely to insert into the host genome or cause other types of genomic perturbations that may result in mutagenesis and tumorogenesis as can be the case with DNA-based technologies. The compositions and methods are also safer than RNA viral vector based technique because, (1) rTeUn rescue and processing do not require viral gene(s) that could create viruses; and (2) rTeUn propagation and expression can be strictly controlled by the presence of the functional NP, L and P proteins. Furthermore, the methods and compositions do not require foreign proteins that exhibit long-term persistence in the host and are unlikely to induce an immune reaction in the host, as can be the case with stable reprogramming methodologies.

The compositions typically include an RNA template unit (rTeUn) which encodes viral regulatory sequences and one or more transgenes of interest. The rTeUn is typically used in combination with the transcription/replication system of a negative strand RNA virus. Preferred negative strand RNA viruses include, but are not limited to, Sendai virus, vesicular stomatitis virus (VSV), and Influenza viruses. General categories include negative-strand RNA-virus families and genome virus families. Representative examples include nonsegmented viruses: Rhabdoviridae Rabies virus, vesicular-stomatitis virus (VSV), Paramyxoviridae Measles virus, mumps virus, human parainfluenza viruses 1, 2 and 3, respiratory syncytial virus (RSV), Sendai virus, rinderpest virus, canine distemper virus, simian virus 5, Filoviridae Ebola virus, Marburg virus, and Unclassified Borna-disease virus; and segmented viruses: Orthomyxoviridae Influenza A, B and C viruses, Bunyaviridae Bunyamwera virus, LaCrosse virus, California encephalitis virus, Rift-Valley-fever virus, hantaviruses, Arenaviridae Lymphocytic choriomeningitis virus (LCMV), Lassa virus, Junin virus, and Argentine haemorrhagic fever. See, Adolfo García-Sastre, *Trends Biotechnol.* 1998 May; 16(5):230-5.

The combination of the rTeUn and viral transcription proteins stabilize and prolong transcription of the transgene, which in turn results in prolonged expression of the protein of interest or functional nucleic acid encoded by the transgene.

A. Recombinant Template Unit

Recombinant template units (rTeUn) and variants thereof are disclosed. rTeUn are typically composed of RNA, but also can include nucleotide analogs and other moieties. The rTeUn can be introduced into cells by different methods, including, but not limited to, liposomal transfection, electroporation, hydronamic shock and nanoparticle-mediated delivery. In addition to a coding sequence, the rTeUn includes negative strand RNA virus regulatory elements that allow the rTeUn to be transcribed by the viral proteins. Therefore, the rTeUn typically include a nucleic acid sequence include negative strand virus transcription recognition elements operably linked to one or more transgenes. As discussed in more detail below, the rTeUn RNA used for transfection is typically produced in vitro from a PCR-produced DNA template. Accordingly, DNA encoding rTeUn, and components and variants thereof are also disclosed.

The rTeUn disclosed herein are coding sequence that in addition to a sequence encoding a gene of interest, typically include viral regulatory elements from a negative strand RNA virus such that when co-transfected into a cell with the viral transcription/replication system from the negative strand RNA virus, the transgene can be transcribed and also replicated. As discussed in more detail below, in some embodiments, the transgene encodes a protein which can be translated in the cell. In other embodiments, the transgene encodes a non-translatable functional nucleic acid, such as an inhibitory nucleic acid.

In some embodiments, in addition to the sequence of the transgene, the rTeUn includes a leader sequence from a negative strand RNA viral, a promoter region of nucleocapsid (NP) gene of a negative strand RNA virus, a terminator region of a large protein (L) gene of a negative strand RNA virus, a trailer from a negative strand RNA virus, a hammerhead ribozyme, and a PolyA tail. In preferred embodiments, the negative stand RNA virus is a SeV. The rTeUn typically includes one or more viral regulatory sequences from Sendai virus (SeV). Sendai virus, which belongs to the family Paramyxoviridae, possesses a single-stranded negative-sense RNA genome. In the genome are at least six genes that encode the nucleoprotein (N, also referred to as NP), phosphoprotein (P), matrix protein (M), fusion protein (F), hemagglutinin-neuraminidase (HN), and large protein (L) from the 3'-to-5' direction, individually flanked by both of the viral regulatory sequences, such as the transcription start and termination sequences. At the 3' end of the genome is the 52-base leader sequence that acts as a promoter for transcription and replication of the viral genome (Lamb, R. A., and D. Kolakofsky, "Paramyxoviridae: the viruses and their replication," p. 1305-1340. In D. M. Knipe and P. M. Howley (ed.), *Fields virology,* 4th ed., vol. 1. Lippincott/Williams & Wilkins, Philadelphia, Pa. (2001)).

Therefore, the rTeUn can include a leader sequence from an SeV, a promoter region from a SeV gene, a terminator region from a SeV gene, the trailer of an SeV, a hammerhead ribozyme, and a PolyA tail.

In some embodiment, rTeUn can include a leader sequence from an SeV, a promoter region from the N gene of an Sev, a terminator region of the L gene in an SeV, the trailer of an SeV, a hammerhead ribozyme, and a PolyA tail. Suitable SeV sequences can be derived from SeV stains and sequences thereof that are known in the art, see, for example, Sendai virus, strain Ohita complete genome, NCBI Reference Sequence: NC_001552.1; Sendai virus strain BB1, complete genome GENBANK® (sequence database) accession number: DQ219803.1; Sendai virus strain Tianjin, complete genome GENBANK® (sequence database) accession number: EF679198.1; Sendai virus genomic RNA, complete genome, strain: pi GENBANK® (sequence database) accession number; Sendai virus genomic RNA, complete genome, strain: Nagoya GENBANK® (sequence database) accession number: AB195968.1; Sendai virus genomic RNA, complete genome, strain Hamamatsu clone: E30M15cl5, viral complementary sequence GENBANK® (sequence database) accession number:

AB065189.1; Sendai virus genomic RNA, complete genome, clone: E30cl2, viral complementary sequence GENBANK® (sequence database) accession number: AB065186.1; Sendai virus genomic RNA, complete genome, clone: E15c12, viral complementary sequence GENBANK® (sequence database) accession number: AB065187.1; Sendai virus genomic RNA, complete genome GENBANK® (sequence database) accession number: AB039658.1; Sendai virus genomic RNA, complete genome, strain: Nagoya 1-60 GENBANK® (sequence database) accession number: AB275417.1; Sendai virus genomic RNA, complete genome, strain: Cl. 151 GENBANK® (sequence database) accession number: AB275416.1; Sendai virus strain Fushimi Taxonomy ID: 11195.

The rTeUn can include a hammerhead ribozyme. A hammerhead ribozyme is an RNA molecule that self-cleaves via a small conserved secondary structural motif termed a "hammerhead." Most hammerhead RNAs are subsets of two classes of plant pathogenic RNAs: the satellite RNAs of RNA viruses and the viroids. Hammerhead ribozymes typically include three base paired helices, separated by short linkers of conserved sequences. The helices are referred to as I, II and III. Hammerhead ribozymes can be classified into three types based on which helix the 5' and 3' ends are found in. If the 5' and 3' ends of the sequence contribute to stem I then it is a type I hammerhead ribozyme, and if the 5' and 3' ends of the sequence contribute to stem III then it is a type III hammerhead ribozyme. The full-length hammerhead ribozymes consist of additional sequence elements in stems I and II that permit additional tertiary contacts to form.

The rTeUn can include a polyA segment. A polyA/T segment of the transcriptional DNA template of the rTeUn can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In some embodiments, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine.

1. Exemplary rTeUn

Typically, a rTeUn including recognition elements from SeV can be transcribed in the presence of the Sendai viral proteins NP, P and L. In some embodiments, the orientation of the rTeUn, referred to herein as, "genomic sequence rTeUn" or "genomic orientation rTeUn" includes from the 5' to 3' direction the following elements: an SeV leader, an SeV promoter region of N gene, a sequence encoding the gene of interest, an SeV terminator region of L gene, an SeV trailer, a hammerhead ribozyme, and a PolyA tail. In some embodiments, the orientation of the rTeUn, referred to herein as, "anti-genomic rTeUn" or "anti-genomic orientation rTeUn" includes from the 3' to 5' direction the following elements: an SeV trailer, an SeV terminator region of L gene, a sequence encoding the gene of interest, an SeV promoter region of N gene, an SeV leader, a hammerhead ribozyme, and a PolyA tail.

As illustrated by the sequences below, in some embodiments, the rTeUn can be described as a first regulatory sequence followed by a transgene followed a second regulatory sequence. The first regulatory sequence, transgene, and second regulatory sequence can be operably linked.

A genomic sequence of a rTeUn can have a first regulatory sequence:

```
                                          (SEQ ID NO: 1)
accaaacaagagaaaaaacatgtatggaatatataatgaagtcagacagg
atttagggtcaaagtatccaccctgaggagcaggttccagaccctttgc
tttgctgccaaagttcacg;
```

followed by a sequence encoding a transgene;
followed by a second regulatory sequence:

```
                                          (SEQ ID NO: 2)
taataattagtccctatcgtgcagaacgatcgaagctccgcggtacctgg
aagtcttggacttatccatatgacaatagtaagaaaaacttacaagaaga
caagaaaatttaaaagaataaatatctcttaaactcttgtctggtggccg
gcatggtcccagcctcctcgctggcgccggctgggcaacattccgagggg
accgtcccctcggtaatggcgaatgggacggatccctgcagctcgagagg
cctaattaattaagtcgacgatccggctgctaacaaagcccgaaaggaag
ctgagttggctgctgccaccgctgagcaataactagcataaccccttggg
gcctctaaacgggtcttgaggggtttttgctgaaaggaggaactatatc
cggatcgaga-PolyA(100b).
```

Nucleotide number 1 through nucleotide number 119 of SEQ ID NO:1 comprise a leader sequence and promoter of NP gene.

Nucleotide number 1 through nucleotide number 145 of SEQ ID NO:2 comprise distal region of SeV with trailer.

Nucleotide number 146 through nucleotide number 229 of SEQ ID NO:2 comprise hepatitis delta virus ribozyme.

Nucleotide number 276 through nucleotide number 410 SEQ ID NO:2 comprise T7 TΦ terminator.

An antigenomic sequence of a rTeUn can have a first regulatory sequence:

```
                                          (SEQ ID NO: 3)
accagacaagagtttaagagatatttattcttttaaattttcttgtcttc
ttgtaagtttttcttactattgtcatatggataagtccaagacttccagg
taccgcggagcttcgatcgttctgcacgatagggactaattatta;
```

followed by a sequence encoding a transgene;
followed by a second regulatory sequence:

```
                                          (SEQ ID NO: 4)
cgtgaactttggcagcaaagcaaagggtctggaacctgctcctcagggtg
gatactttgaccctaaaatcctgtctgacttcattatatattccatacat
gtttttctcttgtttggtggccggcatggtcccagcctcctcgctggcg
ccggctgggcaacattccgaggggaccgtcccctcggtaatggcgaatgg
```

-continued

```
gacggatccctgcagctcgagaggcctaattaattaagtcgacgatccgg

ctgctaacaaagcccgaaaggaagctgagttggctgctgccaccgctgag

caataactagcataaccccttggggcctctaaacgggtcttgaggggttt

tttg-Poly A (100b)

ggccggcatggtcccagcctcctcgctggcgccggctgggcaacattccg

aggggaccgtcccctcggtaatggcgaatgggac.
```

Nucleotide number 1 through nucleotide number 145 of SEQ ID NO:3 comprise a distal region of SeV with trailer.

Nucleotides number 1 through nucleotide number 119 of SEQ ID NO:4 comprise a leader sequence and promoter of NP gene.

Nucleotide number 120 through nucleotide number 203 of SEQ ID NO:4 comprise hepatitis delta virus ribozyme.

Nucleotides number 249 through nucleotide number 354 of SEQ ID NO:4 comprise T7 TΦ terminator.

As discussed above, the rTeUn can be designed to carry a transgene of interest, such as a sequence encoding a polypeptide of interest or a functional nucleic acid, which can be interested between SEQ ID NO:1 and SEQ ID NO:2, or SEQ ID NO:3 and SEQ ID NO:4 to form a single, continuous, functional construct. SEQ ID NO:1, 2, 3, and 4 are provided a DNA PCT template constructs, which can be used to generate RNA rTeUn. Accordingly, it will be appreciated that the RNA sequence encoded by the DNA template are also disclosed herein. Variant and functional fragment thereof with 85%, 90%, 95%, 98%, 99%, or more sequence identity to SEQ ID NO:1, 2, 3, or 4 are also disclosed, Variants can include one or more insertions, deletions, or substitutions relative to SEQ ID NO:1, 2, 3, or 4.

2. Transgene

The rTeUn disclosed herein typically include one or more transgenes. As used herein, "transgene" or "transgenes" refers to the sequence of the rTeUn that is transcribed by a negative strand RNA transcription system. In some embodiments the transgene sequence encodes one or more proteins or functional nucleic acids. The transgene can be monocistronic or polycistronic. In some embodiments, transgene is multigenic. The rTeUn can accommodate a transgene(s) of up to about 15,000 nucleotides. Accordingly, in some embodiments, the rTeUn sequence is about less 500, 1000, 2,000, or more than 2,000 nucleotides in length.

a. Polypeptide of Interest

The transgene(s) can encode one or more polypeptides of interest. The polypeptide can be any polypeptide. For example, the polypeptide of interest encoded by the transgene can be a polypeptide that provides a therapeutic or prophylactic effect to an organism or that can be used to diagnose a disease or disorder in an organism. Preferred genes are genes which are useful for short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. It is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

In some embodiments, the rTeUn includes a selectable marker, for example, a selectable marker that is effective in an eukaryotic cell, such as a drug resistance selection marker. This selectable marker gene can encode a factor necessary for the survival or growth of transformed host cells grown in a selective culture medium. Host cells not transformed with the rTeUn and including the viral proteins necessary to mediate transcription of the rTeUn containing the selection gene will not survive in the culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

In some embodiments, the rTeUn includes a reporter gene. Reporter genes are typically genes that are not present or expressed in the host cell. The reporter gene typically encodes a protein which provide for some phenotypic change or enzymatic property. Examples of such genes are provided in K. Weising et al. *Ann. Rev. Genetics,* 22, 421 (1988). Preferred reporter genes include glucuronidase (GUS) gene and GFP genes. Additional genes including those that produce iPC, interleukins, receptors, transcription factors, and pro- and anti-apoptotic proteins.

Methods of using the compositions for reprogramming cells, and particular sequences of particular transgene(s) useful in such methods are described in more detail below.

b. Functional Nucleic Acids

The transgene(s) can encode a functional nucleic acid. Functional nucleic acids are nucleic acid molecules that have a specific function, such as binding a target molecule or catalyzing a specific reaction. Functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide. Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

Gene expression can also be effectively silenced in a highly specific manner through RNA interference (RNAi). This silencing was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

3. Preparation of rTeUn

The rTeUn RNA disclosed herein are typically prepared by in vitro transcription. As discussed in more detail below with respect to preparation of viral proteins, methods of preparing RNA for transfection into a cell or for addition to an in vitro system are known in the art and available commercially. See, for example, U.S. Published Application Nos. 2008/0260706 and 2011/0165133, and Rabinovich, et al., *Hum. Gene Ther.,* 17(10):1027-35 (2006) which describe methods of RNA production for use in transfection that involves in vitro transcription of PCR generated templates, and commercially available kits such as MEGASCRIPT® (in vitro transcription kit) from INVITROGEN™, and the MMESSAGE MMACHINE® (RNA transcription kit) for T7 or SP6.

B. Viral Proteins

1. Viral Transcriptional System Proteins

As discussed above, the rTeUn are capable of being transcribed, and in some cases translated, in the presence of a negative strand RNA virus transcriptional system. Accordingly, RNA virus transcriptional systems and compositions including RNA viral transcriptional system components are disclosed herein. The compositions can include components of the viral transcriptional systems as proteins, or as nucleic acids that can be expressed and translated into proteins. In some embodiments, the composition includes a vector that expresses the protein(s), mRNA that encodes the protein(s), or combinations thereof. In a preferred embodiment, the negative strand RNA virus is a SeV and the virus transcriptional system includes the nucleoprotein (NP), phosphoprotein (P), and large protein (L) of SeV.

In some embodiments, mRNA encoding the NP, P, and L proteins of SeV are present in the composition or delivered to the cell or in vitro system in an effective amount to mediate transcription of the transgene encoded by the rTeUn. In some embodiments, the sequence of NP, P, and L proteins of SeV are derived from Sendia virus strain Fushima, see for example GENBANK® (sequence database) accession number: M30202.1.

The sequence of the NP protein of an SeV can have the amino acid sequence (EMBL-Bank: X17218.1):

```
                                   (SEQ ID NO: 5)
MAGLLSTFDTFSSRRSESINKSGGGAVIPGQRSTVSVFVLGPSVTDDADK

LFIATTFLAHSLDTDKQHSQRGGFLVSLLAMAYSSPELYLTTNGVNADVK

YVIYNIEKDPKRTKTDGFIVKTRDMEYERTTEWLFGPMVNKSPLFQGQRV

AADPDTLLQTYGYPACLGAIIVQVWIVLVKAITSSAGLRKGFFNRLEAFR

QDGTVKGALVFTGETVEGIGSVMRSQQSLVSLMVETLVTMNTARSDLTTL

EKNIQIVGNYIRDAGLASFMNTIKYGVETKMAALTLSNLRPDINKLRSLI

DTYLSKGPRAPFICILKDPVHGEFAPGNYPALWSYAMGVAVVQNKAMQQY

VTGGTYLDMEMFLLGQAVAKDAESKISSALEDELGVTDTAKERLRHHLAN

LSGGDGAYHEPTGGGAIEVALDNADIDLETEAHADQDARGWGGESGERWA

RQVSGGHFVTLHGAERLEEETNDEDVSDIERRIAMRLAERRQEDSATHGD

EGRNNGVDHDEDDDAAAVAGIGGI,
```

or a variant or functional fragment thereof with 85%, 90%, 95%, 98%, 99%, or more sequence identity to SEQ ID NO:5.

The sequence of the P protein of an SeV can have the amino acid sequence (EMBL-Bank: X170081):

```
                                   (SEQ ID NO: 6)
MDQDAFILKEDSEVEREAPGGRESLSDVIGFLDAVLSSEPTDIGGDRS

WLHNTINTPQGPGSAHRAKSEGEGEVSTPSTQ

DNRSGEESRVSGRTSKPEAEAHAGNLDKQNIHRAFGGRTGTNSVSQ
```

-continued

```
DLGDGGDSGILENPPNERGYPRSGIEDENREMAA

HPDKRGEDQAEGLPEEVRGGTSLPDEGEGGASNNGRSMEPGSSHSA

RVTGVLVIPSPELEEAVLRRNKRRPTNSGSKPLT

PATVPGTRSPPLNRYNSTGSPPGKPPSTQDEHINSGDTPAVRVKDRKP

PIGTRSVSDCPANGRPIHPGLETDSTKKGIGE

NTSSMKEMATLLTSLGVIQSAQEFESSRDASYVFARRALKSANYAEM

TFNVCGLILSAEKSSARKVDENKQLLKQIQESV

ESFRDIYKRFSEYQKEQNSLLMSNLSTLHIITDRGGKTDNTDSLTRSPS

VFAKSKENKTKATRFDPSMETLEDMKYKPDL

IREDEFRDEIRNPLYQERDTEPRASNASRLLPSKEKPTMHSLRLVIESS

PLSRAEKAAYVKSLSKCKTDQEVKAVMELVE

EDIESLTN,
```

or a variant or functional fragment thereof with 85%, 90%, 95%, 98%, 99%, or more sequence identity to SEQ ID NO:6.

The sequence of the L protein of an SeV can have the amino acid sequence (Q06996 (L_SENDF) Reviewed, UniProtKB/Swiss-Prot):

```
                                           (SEQ ID NO: 7)
MDGQESSQNP SDILYPECHL NSPIVRGKIA QLHVLLDVNQ

PYRLKDDSII NITKHKIRNG GLSPRQIKIR SLGKALQRTI

KDLDRYTFDP YPTYSQELLR LDIPEICDKI RSVFAVSDRL

TRELSSGFQD LWLNIFKQLG NIEGREGYDP LQDISTIPEI

TDKYSRNRWY RPFLTWFSIK YDMRWMQKTR PGGPLDTSNS

HNLLECKSYT LVTYGDLVMI LNKLTLTGYI LTPELVLMYC

DVVEGRWNMS AAGHLDKRSI GITSKGEELW ELVDSLFSSL

GEEIYNVIAL LEPLSLALIQ LNDPVIPLRG AFMRHVLTEL

QTVLTSRDVY TDAEADTIVE SLLAIFHGTS IDEKAEIFSF

FRTFGHPSLE AVTAADKVRA HMYAQKAIKL KTLYECHAVF

CTIIINGYRE RHGGQWPPCD FPDHVCLELR NAQGSNTAIS

YECAVDNYTS FIGFKFRKFI EPQLDEDLTI YMKDKALSPR

KEAWDSVYPD SNLYYKAPES EETRRLIEVF INDENFNPEE

IINYVESGDW LKDEKFNISY SLKEKEIKQE GRLFAKMTYK

MRAVQVLAET LLAKGIGELF SENGMVKGEI DLLKRLTTLS

VSGVPRTDSV YNNSKSSEKR NEGMKKKNSG GYWDEKKRSR

HEFKATDSST DGYETLSCFL TTDLKKYCLN WRFESTALFG

QRCNEIFGFK TFFNWMHPVL ERCTIYVGDP YCPVADRMHR

QLQDHADSGI FIHNPRGGIE GYCQKLWTLI SISALHLAAV

RVGVRVSAMV QGDNQAIAVT SRVPVAQTYK QKKNHVYEET

TKYFGALRHV MFDVGHELKL NETIISSKMF VYSKRIYYDG

KILPQCLKAL TRCVFWSETL VDENRSACSN ISTSIAKAIE

NGYSPILGYC IALYKTCQQV CISLGMTINP TISPTVRDQY
```

-continued

```
FKGKNWLRCA VLIPANVGGF NYMSTSRCFV RNIGDPAVAA

LADLKRFIRA DLLDKQVLYR VMNQEPGDSS FLDWASDPYS

CNLPHSQSIT TIIKNITARS VLQESPNPLL SGLFTETSGE

EDLNLASFLM DRKVILPRVA HEILGNSLTG VREAIAGMLD

TTKSLVRASV RKGGLSYGIL RRLVNYDLLQ YETLTRTLRK

PVKDNIEYEY MCSVELAVGL RQKMWIHLTY GRPIHGLETP

DPLELLRGTF IEGSEVCKLC RSEGADPIYT WFYLPDNIDL

DTLTNGSPAI RIPYFGSATD ERSEAQLGYV RNLSKPAKAA

IRIAMVYTWA YGTDEISWME AALIAQTRAN LSLENLKLLT

PVSTSTNLSH RLKDTATQMK FSSATLVRAS RFITISNDNM

ALKEAGESKD TNLVYQQIML TGLSLFEFNM RYKKGSLGKP

LILHLHLNNG CCIMESPQEA NIPPRSTLDL EITQENNKLI

YDPDPLKDVD LELFSKVRDV VHTVDMTYWS DDEVIRATSI

CTAMTIADTM SQLDRDNLKE MIALVNDDDV NSLITEFMVI

DVPLFCSTFG GILVNQFAYS LYGLNIRGRE EIWGHVVRIL

KDTSHAVLKV LSNALSHPKI FKRFWNAGVV EPVYGPNLSN

QDKILLALSV CEYSVDLFMH DWQGGVPLEI FICDNDPDVA

DMRRSSFLAR HLAYLCSLAE ISRDGPRLES MNSLERLESL

KSYLELTFLD DPVLRYSQLT GLVIKVFPST LTYIRKSSIK

VLRTRGIGVP EVLEDWDPEA DNALLDGIAA EIQQNIPLGH

QTRAPFWGLR VSKSQVLRLR GYKEITRGEI GRSGVGLTLP

FDGRYLSHQL RLFGINSTSC LKALELTYLL SPLVDKDKDR

LYLGEGAGAM LSCYDATLGP CINYYNSGVY SCDVNGQREL

NIYPAEVALV GKKLNNVTSL GQRVKVLFNG NPGSTWIGND

ECEALIWNEL QNSSIGLVHC DMEGGDHKDD QVVLHEHYSV

IRIAYLVGDR DVVLISKIAP RLGTDWTRQL SLYLRYWDEV

NLIVLKTSNP ASTEMYLLSR HPKSDIIEDS KTVLASLLPL

SKEDSIKIEK WILIEKAKAH EWVTRELREG SSSSGMLRPY

HQALQTFGFE PNLYKLSRDF LSTMNIADTH NCMIAFNRVL

QDTIFEWARI TESDKRLKLT GKYDLYPVRD SGKLKTISRR

LVLSWISLSM STRLVTGSFP DQKFEARLQL GIVSLSSREI

RNLRVITKTL LDRFEDIIHS ITYRFLTKEI KILMKILGAV

KMFGASQNEY TTVIDDGSLG DIEPYDSS,
```

or a variant or functional fragment thereof with 85%, 90%, 95%, 98%, 99%, or more sequence identity to SEQ ID NO:7.

2. Viral Packaging Proteins

Virus packaging systems and compositions including viral packaging system components are disclosed herein. The compositions can include viral packaging system proteins themselves, or nucleic acids encoding the viral packaging system proteins. For example, in some embodiments the composition includes a vector that expresses the protein(s), exogenous mRNA that encodes the protein(s), or combinations thereof. In a preferred embodiment, the RNA virus is an SeV and the packaging system includes the matrix protein (M), fusion protein (F), and hemagglutinin-neuraminidase (HN).

In some embodiments, mRNA encoding the M, HN, F, proteins of SeV, or combinations thereof, are present in the composition or delivered to the cell or in vitro system in an effective amount to package the rTeUn and associated viral proteins into virus-like particles. In some embodiments, the sequence of the M, HN, and F proteins of SeV are derived from Sendia virus strain Fushimi, The sequence of the M protein of an SeV can have the amino acid sequence P17748 (MATRX_SENDF) Reviewed, UniProtKB/Swiss-Prot

```
                                                (SEQ ID NO: 8)
MADIYRFPKFSYEDNGTVEPLPLRTGPDKKAIPYIRIIKVGDPPKHG

VRYLDLLLLGFFE

TPKQTTNLGSVSDLTEPTSYSICGSGSLPIGVAKYYGTDQELLKACT

DLRITVRRTVRAG

EMIVYMVDSIGAPLLPWSGRLRQGMIFNANKVALAPQCLPVDKDI

RFRVVFVNGTSLGAI

TIAKIPKTLADLALPNSISVNLLVTLKTGISTEQKGVLPVLDDQGEK

KLNFMVHLGLIRR

KVGKIYSVEYCKSKIERMRLIFSLGLIGGISFHVQVTGTLSKTFMSQ

LAWKRAVCFPLMD

VNPHMNLVIWAASVEITGVDAVFQPAIPRDFRYYPNVVAKNIGRIRK

L,
```

or a variant or functional fragment thereof with 85%, 90%, 95%, 98%, 99%, or more sequence identity to SEQ ID NO:8.

The sequence of the EN protein of an SeV can have the amino acid sequence P19758 (HN_SENDF) Reviewed, UniProtKB/Swiss-Prot

```
                                                (SEQ ID NO: 9)
MDGDRGKRDSYWSTSPSGSTTKLASGWERSSKVDTWLLILSFTQWA

LSIATVIICIIISA

RQGYSMKEYSMTVEALNMSSREVKESLTSLIRQEVIARAVNIQSSVQ

TGIPVLLNKNSRD

VIQMIDKSCSRQELTQLCESTIAVHHAEGIAPLEPHSFWRCPVGEPYL

SSDPKISLLPGP

SLLSGSTTISGCVRLPSLSIGEAIYAYSSNLITQGCADIGKSYQVLQLG

YISLNSDMFPD

LNPVVSHTYDINDNRKSCSVVATGTRGYQLCSMPTVDERTDYSSDGI

EDLVLDVLDLKGS

TKSHRYRNSEVDLDHPFSALYPSVGNGIATEGSLIFLGYGGLTTPLQG

DTKCRTQGCQQV

SQDTCNEALKITWLGGKQVVSVIIQVNDYLSERPKIRVTTIPITQNYL
```

-continued

GAEGRLLKLGDR

VYIYTRSSGWHSQLQIGVLDVSHPLTINWTPHEALSRPGNEECNWYN

TCPKECISGVYTD

AYPLSPDAANVATVTLYANTSRVNPTIMYSNTTNIINMLRIKDVQLE

AAYTTTSCITHFG

KGYCFHIIEINQKSLNTLQPMLFKTSIPKLCKAES, or a variant or functional fragment thereof with 85%, 90%, 95%, 98%, 99%, or more sequence identity to SEQ ID NO:9.

The sequence of the F protein of an SeV can have the amino acid sequence (P12575 (FUS_SENDF) Reviewed, UniProtKB/Swiss-Prot)

(SEQ ID NO: 10)

MTAYIQRSQCISTSLLVVLTTLVSCQIPRDRLSNIGVIVDEGKS

LKIAGSHESRYIVLSL

VPGVDLENGCGTAQVIQYKSLLNRLLIPLRDALDLQEALITVT

NDTTQNAGVPQSRFFGA

VIGTIALGVATSAQITAGIALAEAREAKRDIALIKESMTKTHKS

IELLQNAVGEQILALK

TLQDFVNDEIKPAISELGCETAALRLGIKLTQHYSGLLTAFGSN

FGTIGEKSLTLQALSS

LYSANITEIMTTIRTGQSNIYDVIYTEQIKGTVIDVDLERYMVT

LSVKIPILSEVPGVLI

HKASSISYNIDGEEWYVTVPSHILSRASFLGGADITDCVESRLT

YICPRDPAQLIPDSQQ

KCILGDTTRCPVTKVVDSLIPKFAFVNGGVVANCIASTCTCGT

GRRPISQDRSKGVVFLT

HDNCGLIGVNGVELYANRRGHDATWGVQNLTVGPAIAIRPID

ISLNLADATNFLQDSKAE

LEKARKILSEVGRWYNSRETVITIIVVMVVILVVIIVIVIVLYRL

KRSMLMGNPDDRIPR

DTYTLEPKIRHMYTNGGFDAMAEKR, or a variant or functional fragment thereof with 85%, 90%, 95%, 98%, 99%, or more sequence identity to SEQ ID NO:10.

3. Preparation of Viral mRNA and Proteins a. In Vitro Transcription

In some embodiments, mRNA of viral protein(s) of the viral transcription system, packaging system, or combination thereof are prepared by in vitro transcription. Methods of preparing RNA for transfection into a cell or for addition to an in vitro system are known in the art and available commercially. See, for example, U.S. Published Application Nos. 2008/0260706 and 2011/0165133, and Rabinovich, et al., *Hum. Gene Ther.*, 17(10):1027-35 (2006) which describe methods of RNA production for use in transfection that involves in vitro transcription of PCR generated templates. The constructs can include 3' and 5' untranslated sequence ("UTR"), a 5' cap and/or Internal Ribosome Entry Site (IRES), the gene to be expressed, and a polyA tail, typically 100-500 bases in length.

DNA of interest from any source can be directly converted by PCR into a template for in vitro RNA synthesis using appropriate primers and RNA polymerase. The source of the DNA can be, for example, genomic DNA, plasmid DNA, phage DNA, cDNA, synthetic DNA sequence or any other appropriate source of DNA containing the coding sequence of the viral protein of interest. The gene can include some or all of the 5' and/or 3' untranslated regions (UTRs).

PCR can used to generate a template for in vitro transcription of RNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), or rTeUn including 5' and 3' UTRs. The primers can also be designed to amplify a portion of a gene that encodes a particular domain of interest. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

i. Untranslated Regions

Chemical structures with the ability to promote stability and/or translation efficiency may also be used. The RNA preferably has 5' and 3' UTRs. The length of the 3' UTR can be 100 nucleotides or less, or exceed 100 nucleotides. In some embodiments mRNA with 3' UTR greater than 100 nucleotides are translated more efficiently than mRNA with less than 100 nucleotides of 3' UTR. In some embodiments the 3' UTR sequence is between 100 and 5000 nucleotides. The length of the 5' UTR is not as critical as the length of the 3' UTR and can be shorter. In one embodiment, the 5' UTR is between zero and 3000 nucleotides in length. The length of 5' and 3' UTR sequences to be added to the coding region can be altered by different methods, including, but not limited to, PCR. Using this approach, one of ordinary skill in the art can modify the 5' and 3' UTR lengths required to achieve optimal translation efficiency following transfection of the transcribed RNA.

The 5' and 3' UTR can be heterologous UTRs. In some embodiments, the UTR are derived from host gene, such as an actively expressed host gene, to ensure sufficient translation of the mRNA in the host. UTR sequences that are not endogenous can be added by incorporating the UTR sequences by PCR or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain a Kozak sequence. For example, when a 5' UTR that is not endogenous to the gene of interest is being added by PCR as described above, a consensus Kozak sequence can be included, or redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

ii. RNA Polymerase Promoter

To enable synthesis of RNA from a DNA template without the need for gene cloning, a promoter of transcription should be attached to the DNA template upstream of the sequence to be transcribed. Bacteriophage RNA polymerase promoter sequences can be attached to DNA by different genetic engineering methods, such as DNA ligation, or can be added by PCR to the forward primer (5') of the sequence that is substantially complementary to the target DNA. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described above. Other useful promoters include, but are not limited to, T3 and SP6 RNA polymerase promoters. Consensus nucleotide sequences for T7, T3 and SP6 promoters are known in the art.

iii. Poly(A) Tail and 5' Cap

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, *Nuc Acids Res.,* 13:6223-36 (1985); Nacheva and Berzal-Herranz, *Eur. J. Biochem.,* 270:1485-65 (2003). This could lead to runoff transcript bending followed by template exchange with the second DNA strand or transcription of RNA itself (Triana-Alonso et al., *J. Biol. Chem.,* 270:6298-307 (1995); Dunn and Studier, *J. Mol. Biol.,* 166:477-535 (1983); Arnaud-Barbe et al., *Nuc. Acids Res.,* 26:3550-54 (1998); Macdonald et al., 1993), and then to the aberrant transcription in a reverse direction and accumulation of double stranded RNA, which can inhibit gene expression. DNA linearization itself is not sufficient for correct transcription (Triana-Alonso et al., *J. Biol. Chem.,* 270:6298-307 (1995); Dunn and Studier, *J. Mol. Biol.,* 166:477-535 (1983); Arnaud-Barbe et al., 1998 *Nuc. Acids Res.,* 26:3550-54 (1998); Macdonald et al., *J. Mol. Biol.,* 232:1030-47 (1993); Nakano et al., *Biotechnol. Bioeng.,* 64:194-99 (1999). Plasmid DNA linearized downstream of a poly(A/T) stretch of 64-100 nucleotides results in good templates (Saeboe-Larssen et al., *J. Immunol. Meth.,* 259:191-203 (2002); Boczkowski et al., *Cancer Res.,* 60:1028-34 (2000); Elango et al., *Biochem Biophys Res Commun.,* 330:958-966 2005). An endogenous termination signal for T7 RNA polymerase encodes an RNA that can fold into a stem-loop structure followed by a track of uridine residues (Dunn and Studier, *J. Mol. Biol.,* 166:477-535 (1983); Arnaud-Barbe et al., 1998 *Nuc. Acids Res.,* 26:3550-54 (1998)).

Even without a hairpin, a track of synthesized uridines can attenuate transcription (Kiyama and Oishi, *Nucleic Acids Res.,* 24:4577-4583 (1996).

It was hypothesized that the linearization of plasmid DNA downstream of the poly(A/T) stretch probably formed a type of "dynamic" terminator preventing potential aberrant transcription: a 3' extension of the RNA transcript over a poly(A/T) stretch and transcription in the reverse direction will create a growing termination-like signal—an extended poly(U) stretch and a poly(A/U) hairpin. Based on this presumption, reversed PCR primers were designed with a 3' anchoring sequence downstream of the coding sequence and a 5' 100 base stretch of poly(T) (Rabinovich et al., 2006).

The polyA/T segment of the transcriptional DNA template can contain 50-5000 bp. It can be produced by PCR by any other method, including, DNA ligation or in vitro recombination.

Poly(A) tails provide stability to RNAs and reduce their degradation. Generally, the length of a poly(A) tail positively correlates with the stability of the transcribed RNA. In one embodiment, the poly(A) tail is between 100 and 5000 adenosines. A 100 base pair stretch of poly(A) is sufficient to enable efficient translation of an RNA transcript.

Poly(A) tails of RNAs can be further extended following in vitro transcription with the use of a poly(A) polymerase, such as *E. coli* polyA polymerase (E-PAP). The examples below demonstrate that increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine.

5'caps on also provide stability to RNA molecules. In a preferred embodiment, RNAs produced by the methods disclosed herein include a 5' cap. The 5' cap may, for example, be $m^7G(5')ppp(5')G$, $m^7G(5')ppp(5')A$, G(5')ppp(5')G or G(5')ppp(5')A cap analogs, which are all commercially available. The 5' cap can also be an anti-reverse-cap-analog (ARCA) (Stepinski, et al., RNA, 7:1468-95 (2001)) or any other suitable analog. The 5' cap is provided using techniques known in the art and described herein (Cougot, et al., *Trends in Biochem. Sci.,* 29:436-444 (2001); Stepinski, et al., *RNA,* 7:1468-95 (2001); Elango, et al., *Biochem. Biophys. Res. Commun.,* 330:958-966 (2005)).

The RNAs can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

Kits for in vitro transcription of constructs encoding mRNA useful in the compositions and methods are commercially available, see for example, MEGASCRIPT® (in vitro transcription kit) from INVITROGEN™, and the MMESSAGE MMACHINE® (RNA transcription kit) for T7 or SP6.

b. Vectors Expressing Viral Proteins

In some embodiments, one or more vectors encoding the viral protein(s) are present in the composition or delivered to the cell or in vitro system. In some embodiments the viral proteins are expressed from an expression vector. Nucleic acids, such as those described above, can be inserted into vectors for expression in cells or in vitro systems. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. Operably linked means the disclosed sequences are incorporated into a genetic construct so that expression control sequences effectively control expression of a sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II).

Some promoters are "constitutive," and direct transcription in the absence of regulatory influences. Some promoters are "tissue specific," and initiate transcription exclusively or selectively in one or a few tissue types. Some promoters are "inducible," and achieve gene transcription under the influence of an inducer. Induction can occur, e.g., as the result of a physiologic response, a response to outside signals, or as the result of artificial manipulation. Some promoters respond to the presence of tetracycline; "rtTA" is a reverse tetracycline controlled transactivator. Such promoters are well known to those of skill in the art. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Host cells can be genetically engineered (e.g., transformed, transduced or transfected) with the vectors encoding viral protein(s), which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)).

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

c. Recombinant Viral Proteins

In some embodiments, viral protein(s) of the viral transcription system, packaging system, or combinations thereof are present in the composition or delivered to the cell or in vitro system as an effective amount of viral protein(s) to mediate transcription of the transgene encoded by the rTeUn. In some embodiments, the sequence of the viral protein(s) is modified to include a protein transduction domain, signal targeting signal or a combination thereof to enhance transport of the fusion protein across lipid membranes, for example across the plasma membrane of a cell. Accordingly, in some embodiments, one or more of the viral proteins are fusion proteins.

i. Protein Transduction Domains

Protein transduction domains (PTD), also known as cell penetrating peptides (CPPS). PTDs are known in the art, and include, but are not limited to, small regions of proteins that are able to cross a cell membrane in a receptor-independent mechanism (Kabouridis, P., *Trends in Biotechnology* (10: 498-503 (2003)). Although several of PTDs have been documented, the two most commonly employed PTDs are derived from TAT (Frankel and Pabo, *Cell,* 55(6):1189-93 (1988)) protein of HIV and Antennapedia transcription factor from *Drosophila*, whose PTD is known as Penetratin (Derossi et al., *J Biol Chem.,* 269(14):10444-50 (1994)).

The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRRR (SEQ ID NO:11)) of the parent protein that appears to be critical for uptake. Additionally, the basic domain Tat(49-57) or RKKRRQRRR (SEQ ID NO:12) has been shown to be a PTD. TAT has been favored for fusion to proteins of interest for cellular import. Several modifications to TAT, including substitutions of Glutamine to Alanine, i.e., Q→A, have demonstrated an increase in cellular uptake anywhere from 90% (Wender et al., *Proc Natl Acad Sci USA.,* 97(24): 13003-8 (2000)) to up to 33 fold in mammalian cells. (Ho et al., *Cancer Res.,* 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include, but are not limited to, poly-Arg RRRRRRR (SEQ ID NO:13); PTD-5-RRQRRTSKLMKR (SEQ ID NO:14); Transportan GWTLNSAGYLLGKINL-KALAALAKKIL (SEQ ID NO:15); KALA-WEAKLAKA-LAKALAKHLAKALAKALKCEA (SEQ ID NO:16); and RQIKIWFQNRRMKWKK (SEQ ID NO:17).

In some embodiments, the fusion protein includes an endosomal escape sequence that improves delivery of the protein to the interior of the cell. Endosomal escape sequences are known in the art, see for example, Barka, et al., *Histochem. Cytochem.,* 48(11):1453-60 (2000) and Wadia and Stan, *Nat. Med.,* 10(3):310-5 (2004).

ii. Targeting Signal or Domain

In some embodiments, the viral protein(s) is optionally modified to include one or targeting signals or domains. The targeting signal or sequence can be specific for a host, tissue, organ, cell, organelle, an organelle such as the nucleus, or cellular compartment. Moreover, the compositions disclosed here can be targeted to other specific intercellular regions, compartments, or cell types.

In some embodiments, the targeting signal binds to a ligand or receptor which is located on the surface of a target cell such as to bring the fusion protein and cell membranes sufficiently close to each other to allow penetration of the fusion protein into the cell. Additional embodiments are directed to specifically delivering the fusion protein to specific tissue or cell types.

In a preferred embodiment, the targeting molecule is selected from the group consisting of an antibody or antigen binding fragment thereof, an antibody domain, an antigen, a cell surface receptor, a cell surface adhesion molecule, a viral envelope protein and a peptide selected by phage display that binds specifically to a defined cell.

Targeting domains to specific cells can be accomplished by modifying the disclosed fusion proteins to include specific cell and tissue targeting signals. These sequences target specific cells and tissues, but in some embodiments the interaction of the targeting signal with the cell does not occur through a traditional receptor: ligand interaction. The eukaryotic cell includes a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the fusion protein can be altered by changing the targeting signal. In one specific embodiment, fusion proteins are provided that enable the addition of cell surface antigen specific antibodies to the fusion protein for targeting fusion protein.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest iii. Expressing and Purifying Recombinant Proteins Methods of expressing recombinant proteins and isolating recombinant proteins in various recombinant expression systems including bacteria, yeast, insect, and mammalian cells are known in the art, see, for example, *Current Protocols in Protein Science* (Print ISSN: 1934-3655 Online ISSN: 1934-3663, Last updated January 2012). Useful prokaryotic and eukaryotic systems for expressing and producing polypeptides are well known in the art and include, for example, *Escherichia coli* strains such as BL-21 and cultured mammalian cells such as CHO cells.

In eukaryotic host cells, a number of viral-based expression systems can be utilized to express viral protein(s). Viral based expression systems are well known in the art and include, but are not limited to, baculoviral, SV40, retroviral, or vaccinia based viral vectors.

Mammalian cell lines that stably express proteins can be produced using expression vectors with appropriate control elements and a selectable marker. For example, the eukaryotic expression vectors pCR3.1 (Invitrogen Life Technologies) and p91023(B) (see Wong et al. (1985) *Science* 228: 810-815) are suitable for expression of recombinant proteins in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NS0 system). The transfected cells can be cultured such that the polypeptide of interest is expressed, and the polypeptide can be recovered from, for example, the cell culture supernatant or from lysed cells.

Recombinant proteins can be isolated using, for example, chromatographic methods such as affinity chromatography, ion exchange chromatography, hydrophobic interaction chromatography, DEAE ion exchange, gel filtration, and hydroxylapatite chromatography. In some embodiments, recombinant proteins can be engineered to contain an additional domain containing amino acid sequence that allows the polypeptides to be captured onto an affinity matrix. For example, an Fc-containing polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify recombinant proteins. Recombinant proteins can additionally be engineered to contain a secretory signal (if there is not a secretory signal already present) that causes the protein to be secreted by the cells in which it is produced. The secreted proteins can then conveniently be isolated from the cell media.

d. Genomic Integration of Genes Encoding Viral Proteins

As discussed above, one of the advantages of the rTeUn system is that it does not require stable transfection or integration viral sequences into the host or target cell's genome. Nevertheless, in some embodiments one or more of the viral proteins necessary for transcription of the rTeUn or for packaging of the nucleoprotein-rTeUn complex can be integrated in the genome of a host cell. Accordingly, in some embodiments, when negative strand RNA virus is SeV, genes encoding the NP, P, L, F, M, or HN proteins or combinations thereof can be incorporated into a host cells. Methods of engineering a microorganism or cell line to incorporate a nucleic acid sequence into its genome are known in the art. In some embodiments, the transformed cells are used to generate recombinant viral proteins for use in the compositions and methods. In some embodiments, the transformed cells are the target cells, which are subsequently reprogrammed by introduction of rTeUn.

III. Methods of Use

A. Methods of Transfecting Cells with rTeUn

When rTeUn is transfected into a cell in the presence of a suitable viral transcriptional system, the transgene encoded by the rTeUn is replicated and the transgene encoded by the rTeUn is transcribed into mRNA or functional nucleic acid. The combination of the rTeUn and viral transcriptional proteins prolong expression of the transgene, which in turn results in prolonged, but transient, expression of the protein of interest or functional nucleic acid encoded by the transgene relative to conventional exogenous RNA. For example, when present in a cell with NP, P, and L proteins from SeV, an rTeUn including SeV recognition elements is encapsidated in a nucleoprotein complex, which makes the rTeUn RNA highly resistant to nuclease degradation. P and L proteins form a PL complex that can carry out at least two enzymatic activities: NP-RNA dependent RNA polymerase and NP-RNA dependent transcriptase. The PL complex recognizes viral elements of the NP-encapsidated rTeUn and transcribes the transgene into mRNA, or a functional nucleic acid. If the transgene encodes a polypeptide, the host cell's translation system can recognize the mRNA and translate the mRNA into a polypeptide.

For example, a method of expressing a transgene in a cell can include introducing into the cell rTeUn in combination with a virus transcriptional system including the NP, P, and L proteins of SeV, or one or more nucleic acid constructs encoding the NP, P, and L proteins of SeV which can be translated by the cell's translational system, where the rTeUn and virus transcriptional system are present in the cell in an effective amount for the transgene to be transiently expressed in the cell. As discussed in more detail below, in some embodiments, the method is employed to reprogram the cell. In some embodiments, the nucleoprotein complex is packaged into virus-like particles (VLPs) by packaging proteins such as F, M, of HN of SeV or similar proteins of other negative strand RNA viruses. M protein determines viral particle assembly and budding. HN and F proteins mediate attachment of viral particles and the penetration of viral ribonucleoprotein complexes into transduced cells. VLPs containing can be used to deliver rTeUn nucleoprotein with high efficiency in various human and animal cells. A packaging system can be obtain from a cell line where rTeUn RNA has been rescued with supplemental mRNAs by adding packaging proteins as describe above (M, F, HN proteins or their encoding mRNAs). Packaging proteins can be introduced by mRNA mediated transfection or by direct introduction of M, F, NH proteins.

Alternatively, cells expressing packaging proteins (such as cells described by Yoshizaki, et al., *J Gene Med.,* 8(9): 1151-9 (2006)) can be used as host cells for preparation and packaging of rTeUn VLPs. Cells can be stably transduced or transfected with packaging protein expression vectors, or genes encoding the packaging proteins can be integrated into the genome of the host cell. Such a system can be used to generate viral-like particles able to efficiently introduce a rTeUn RNA complex into a population of recipient cells. If accompanied by parallel introduction of NP, P and L proteins (as translatable mRNAs or proteins per se), such procedures can lead to highly efficient transfer of a desirable transgene or set of transgenes into different cell populations.

For example, it is known that viral-like particles obtain from the Sendai packaging system are highly infectious and can provide efficient RNA transfer into various type of primary human and animal cells. It is also known that transfection of multiple mRNAs is also very efficient and almost the whole cell population can be transfected with multiple mRNAs (Rabinovich, et al., *Human Gene Therapy,* 20(1): 51-61 (2009) and Rabinovich, et al., *Human Gene Therapy,* 17(10): 1027-35 (2006). Therefore transfection of cells with virus-like particles and mRNAs coding NP, P and L proteins can be efficient and provide transfer and expression of desirable transgenes in most cells. By varying particles/cell ratios one can obtain virtually whole cells populations that are transduced with a transgene.

The viral transcriptional system, packaging proteins, and combinations thereof can be introduced into a host cell as exogenous mRNA encoding the viral protein(s); as one or more expression vectors encoding the viral protein(s); as viral protein(s) or combinations thereof. The mRNA, expression vectors, or proteins components can be part of a single composition with the rTeUn, or the components can be part of separate compositions. For example, in some embodiments, the rTeUn and mRNA encoding one or more viral transcriptional system proteins such as NP, P, and L proteins from an SeV are part of a single compositions and introduced into a target cell at the same time. Alternatively, the rTeUn and mRNA encoding one or more viral transcriptional system proteins such as NP, P, and L proteins from an SeV can be introduced into separately.

RNA, such as the rTeUn and viral mRNAs disclosed herein, can be introduced into target cells using different methods, for example, commercially available methods which include, but are not limited to, electroporation (Amaxa NUCLEOFECTOR™ II (transfection device) (Amaxa Biosystems, Cologne, Germany)), (ECM 830 (BTX) (Harvard Instruments, Boston, Mass.) or the Gene Pulser II (BioRad, Denver, Colo.), Multiporator (Eppendorf, Hamburg Germany), cationic liposome mediated transfection using lipofection, polymer encapsulation, peptide mediated transfection, or biolistic particle delivery systems such as "gene guns" (see, for example, Nishikawa, et al. *Hum Gene Ther,* 12(8):861-70 (2001). In preferred embodiments, the compositions are transfected into cells by lipofection with LIPOFECTINE® (transfection reagent) and LIPOFECTAMINE® (transfection reagent) or by nucleoporation.

The methods also provides the ability to control the level of expression over a wide range by changing the amount of input RNA, making it possible to individually regulate the expression level of each transfected gene. It is also possible to transfect cells with multiple distinct rTeUn simultaneously.

For example, the population of cells can be transfected with one or more distinct rTeUn each encoding one or more distinct mRNAs, one or more distinct functional nucleic acids, or combinations thereof. A population of cells can be transfected with multiple rTeUn simultaneously in a single administration, or multiple administrations can be staggered minutes, hours, days, or weeks apart. Transfection of multiple distinct rTeUn may be staggered. For example, it may be desirable for a first RNA to be expressed prior to expression of one or more additional RNAs.

Furthermore, the PCR-based technique of mRNA production facilitates the design of mRNAs with different structures and domain combinations. For example, chimeric receptor mRNAs can be designed with different structures and combination of their domains. Varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

The level of expression of the transfected RNA can be manipulated over a wide range by changing the amount of input RNA, making it possible to individually regulate the expression level of each transfected RNA. The effective amount of input RNA is determined based on the desired result.

Figure 6:
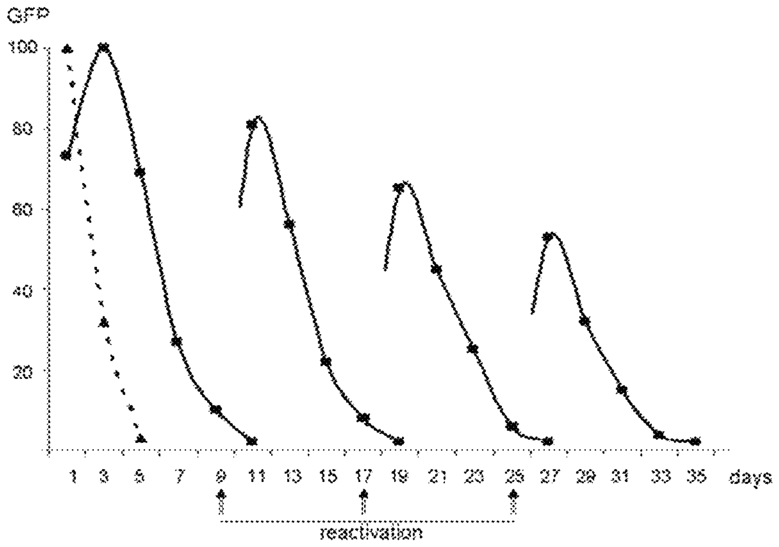
FIG. 6 is a line graph showing the fluorescence (%) of cells following repeated reactivation of GFP rTeUn+ cells with supplemental mRNAs over time (days).

Furthermore, as shown in the Examples below, the rTeUn can be reactivated by adding additional viral transcription proteins. As discussed above, the rTeUn is more stable and characterized by a longer half-life than conventional exogenous mRNA. It has been discovered that expression of a polypeptide encoded by the rTeUn transgene declines before the rTeUn RNA is a degraded. It is believed that expression of the transgene is limited by the shorter-half of the viral transcriptional proteins, which is typically delivered to the cell as viral protein, or conventional exogenous mRNA. For example, when rTeUn is transfected into a host cell in combination with exogenous viral transcriptional system proteins or exogenous mRNA encoding viral transcriptional system proteins, the exogenous protein or mRNA limit the duration of expression of the transgene encoded by the rTeUn, because the mRNA and proteins degrade more quickly than the rTeUn. Therefore, expression of the transgene encoded by the rTeUn, for example a polypeptide of interest, can be reactivated by introducing additional exogenous viral transcriptional system proteins or exogenous mRNA encoding viral transcriptional system proteins. This process of re-introducing viral protein or mRNA encoding viral protein into the cell to re-induce or increase expression of the rTeUn transgene after an initial introduction of viral protein or mRNA encoding viral protein into the cell is referred to herein as "reactivating" or "reactivation." Example 4 and FIG. 6 show that in one experiment, rTeUn was reactivated up to 3 times and expression of the polypeptide encoded by the rTeUn was sustained for at least 35 days in culture. Expression of the rTeUn can be reactive 1, 2, 3, 4, 5 or more times.

As illustrated in the Examples below, it is believed that only part of some cell populations can be reactivated, probably because of spontaneous elimination of rTeUn in growing cells. However, if the rUnTe construct contains selective markers, such as NEO, the cell population can be purified from rTeUn-free cells. Without reactivation, the viral proteins gradually disappear and the rTeUn construct is degraded by RNA degradation machinery. This ensures that the presence and expression of rTeUn in cells can be tightly regulated.

Transfection with rTeUn constructs can be used for relatively long term cell reprogramming, much longer then reprogramming with conventional exogenous mRNAs, but while maintaining similar levels of safety. The use of viral-like particles, as discussed above, can make the procedure quite simple and effective. The use of repeated/multiple reactivations can be quite helpful in methods where long-term reprogramming is crucial. For example RNA transfection has been shown to be the most effective method for the production of induced pluripotent stem cells (iPS) cells from differentiated cells by in vitro 'epigenetic" reprogramming (Warren, et al., *Cell Stem Cell,* 7 (5):618-630 (2010)). However this procedure required multiple rounds of RNA transfection. Use of the rTeUn system can simplify the procedure by decreasing the frequency mRNA transfection.

B. Applications

The rTeUn and viral mRNAs or proteins can be delivered into different types of eukaryotic cells as well as into tissues and whole organisms using transfected cells as carriers or cell-free local or systemic delivery of encapsulated, bound or naked RNA, protein, or combinations thereof. The method can be used to deliver genes or inhibitory nucleic acids into cells not, or only poorly, transfectable for DNA, in vitro and in vivo, and modulate cell activity. The method can be used for any purpose where transient expression is required or sufficient. The disclosed method can be applied to modulation of cell activity in basic research and therapy, in the fields of cancer, stem cells, acute and chronic infections, and autoimmune diseases, including modulation of the developmental pathways.

In some embodiments, the technology is used for personalized therapy. For example, for treatment of tumors, the patient's blood or cells would be collected by an appropriate method such as apheresis, biopsy or venapuncture. The cells would be cultured for at least 24 hours during which time the cells are transfected with an appropriate construct to treat the tumor. The cells can be stored frozen before transfection, if necessary. These are then returned and administered back to the patient.

RNAs useful in the methods are known in the art, and will be selected based on the target host cell type as well as the pathway or cellular activity to be manipulated, or the therapeutic application.

Cells suitable for use with the method include, but are not limited to, primary cells and established cell lines, embryonic cells, immune cells, stem cells, and differentiated cells including, but not limited to, cells derived from ectoderm, endoderm, and mesoderm, including fibroblasts, parenchymal cells, hematopoietic cells, and epithelial cells. As used herein, stem cells include unipotent cells, multipotent cells, and pluripotent cells; embryonic stem cells, and adult stem cells such as hematopoietic stem cells, mesenchymal stem cells, epithelial stem cells, and muscle satellite cells. In one embodiment, somatic cells are de-differentiated or reprogrammed. Any suitable somatic cell can be used. Representative somatic cells include fibroblasts, keratinocytes, adipocytes, muscle cells, organ and tissue cells, and various blood cells including, but not limited to, hematopoietic cells including hematopoietic stem cells, and cells that provide short- or long-term hematopoietic engraftment. The most preferred cell types include, but are not limited to, human fibroblasts, keratinocytes and hematopoietic stem cells. The methods are particularly useful reprogramming cells without permanent alteration of cells' genomes.

1. Immunomodulation

Genetic transduction of different types of cytotoxic lymphocytes to express desired receptors for adoptive immunotherapy is a valuable method to redirect the specificity of lymphocytes for tumor antigens, which are not readily recognized by the endogenous T-cell or NK receptors. However, a potential disadvantage of such method is genome integration of transgenes as well as the technical complexity of the method. It takes weeks or months to clone and accumulate a desirable homogeneous specific lymphocyte population suitable for the treatment. Another problem of cloning is that lymphocyte diversity, an important factor which determines immune response, is an unavoidable complication of such procedure. Cytotoxic lymphocytes are presented as heterogeneous subpopulations such as CD8+, CD4+, CD3+CD56+(CIK) T cells and CD3− CD56+ NK cells, with additional sub diversity among each of subpopulation. The whole cytotoxic potential can be influenced by cooperation of different cell types.

The RNA transfection compositions can be delivered and expressed into the lymphocytes after brief in vitro cell activation, as a minimal expressing cassette. In these conditions genome integration of the transgene is quite improbable. Cell cloning becomes unnecessary because of the efficiency of mRNA transfection and its ability to uniformly modify the entire lymphocyte population. Moreover, different types of lymphocytes such as CD3+CD8+, CD3+CD4+ T cells and Cd56+ CIK and NK cells can be simultaneously transfected with rTeUN and used together to increase their potential synergistic effect. Thus, cells containing an RNA construct introduced according to the disclosed method can be used therapeutically.

For example, a lymphocyte cell population could be withdrawn from a patient, transfected with a combination of rTeNu constructs designed to condition the cells to target cancer cells and viral transcriptional system proteins, and then reintroduced into the patient. The transfected cell population would then target the cancer cells. A benefit of the use of mRNA transfected cells is that mRNA transgene has a limited half-life. The encoded protein will only be produced by the transfected cell for a limited period of time. This may reduce unintended consequences when genetically modified cells are reintroduced into a patient.

It is possible to transfect cells with multiple distinct rTeUn simultaneously. For example, it is possible to generate an autologous lymphocyte population with multiple sets of receptors to recognize and destroy targets which otherwise escape cytotoxic T lymphocyte (CTL) surveillance or to increase the specificity of the CTL towards selected targets. Similar procedures could be used with NK or NKT cells or other types of immune effector cells to target them to specific cells or tissues or increase their avidity for specific cells or tissues. The method can also be used to introduce various mRNAs and/or functional nucleic acids that render the T cell resistant to inhibitory molecules in vivo. Also, mRNAs that encode transcription factors and/or effector proteins characteristic of $CD8^+$ cytotoxic T cells can be introduced into a mixed population of T lymphocytes in order to convert them all to a cytotoxic T cell phenotype.

2. De-differentiating Cells

The methods can be used to de-differentiate, re-differentiate, or re-program cells. The methods are useful for expressing one or multiple RNAs in different cell populations such as fully differentiated cells, partially differentiated cells, such as multipotent cells and non-differentiated cells, such as pluripotent cells. For example, cells can be induced to form induced pluripotent stem (iPS) cells. Constructs useful for de-differentiating cells, for example, converting adult, differentiated somatic cells into stem cells, can be constructed based on known genes, mRNAs, or other nucleotide or protein sequences. See, for example, Yu, et al., *Science,* 318:1917-1920 (2007) and Yamanaka, *Cell Prolif.,* 41:51-56 (2008), which describes induced pluripotent stem (iPS) cells obtained from differentiated primary cells by ectopic expression of combinations of transcription factors such as OCT4, SOX2, NANOG, and LIN28, or OCT3/4, SOX2, KLF4 and c-MYC.

Exemplary genomic, mRNA (cDNA), and protein sequences for OCT4 are known in the art, see, for example, (OCT4) POU5F1 POU class 5 homeobox 1 [*Homo sapiens*] Gene ID: 5460, which provides mRNA (cDNA) sequences GENBANK® (sequence database) accession no. NM_001173531.1 entitled *Homo sapiens* POU class 5 homeobox 1 (POU5F1), transcript variant 3, mRNA; GENBANK® (sequence database) accession no. NM_002701.4 entitled *Homo sapiens* POU class 5 homeobox 1 (POU5F1) transcript variant 1, mRNA; and GENBANK® (sequence database) accession no. NM_203289.4 entitled *Homo sapiens* POU class 5 homeobox 1 (POU5F1), transcript variant 2, mRNA. Exemplary genomic, mRNA (cDNA), and protein sequences for SOX2 are also known in the art, see, for example, SOX2 SRY (sex determining region Y)-box 2 [*Homo sapiens*], Gene ID: 6657, which provides mRNA (cDNA) sequence GENBANK® (sequence database) Accession no. NM_003106.2 entitled mRNA sequence *Homo sapiens* SRY (sex determining region Y)-box 2 (SOX2), mRNA. Exemplary genomic, mRNA (cDNA), and protein sequences for NANOG are also known in the art, see for example NANOG Nanog homeobox [*Homo sapiens*], Gene ID: 79923, which provides the mRNA (cDNA) sequence GENBANK® (sequence database) accession no. NM_024865.2 entitled *Homo sapiens* Nanog homeobox (NANOG), mRNA. Exemplary genomic, mRNA (cDNA), and protein sequences for LIN28 are also known in the art, see for example LIN28A lin-28 homolog A (*C. elegans*) [*Homo sapiens*], Gene ID: 79727, which provides the mRNA (cDNA) sequence GENBANK® (sequence database) accession no. NM_024674.4 entitled *Homo sapiens* lin-28 homolog A (*C. elegans*) (LIN28A), mRNA. Exemplary genomic, mRNA (cDNA), and protein sequences for KLF4 are known in the art, see, for example, KLF4 Kruppel-like factor 4 (gut) [*Homo sapiens*], Gene ID: 9314, which provides the mRNA (cDNA) sequence GENBANK® (sequence database) accession no. NM_004235.4 entitled *Homo sapiens* Kruppel-like factor 4 (gut) (KLF4), mRNA. mRNA sequences for MYC are also known in the art, see for example MYC v-myc myelocytomatosis viral oncogene homolog (avian) [*Homo sapiens*], Gene ID: 4609, which provides the mRNA (cDNA) sequence GENBANK® (sequence database) accession no. NM_002467.4 entitled *Homo sapiens* v-myc myelocytomatosis viral oncogene homolog (avian) (MYC), mRNA.

Following transfection with one or more RNAs, the cells can be maintained or expanded in culture. Methods for culturing both transfected and non-transfected cells are known in the art, and may include providing additional reagents or supplements to enhance viability and/or growth, for example, growth factors or a feeder layer of cells.

Although transfection using the disclosed mRNAs is transient, once the cells have been induced to de-differentiate, the de-differentiated cells can be maintained in their induced state using tissue culture conditions that are known in the art. For examples, differentiated somatic cells such as fibroblasts that are induced to de-differentiate into iPS cells can be maintained as iPS cells using methods consistent with culturing undifferentiated iPS cells.

The method can also be widely used for re-differentiating or reprogramming of cells, for example, to produce iPS cells that can be further modulated to form hematopoietic stem cells, mesenchymal stem cells, epithelial stem cells, and muscle satellite cells; or differentiated cells of human tissues, including, but not limited to, red blood cells, white blood cells including lymphocytes, platelets, stromal cells, fat cells, bone cells including osteoclasts, epithelial tissue including skin cells, muscle tissue including smooth muscle, skeletal muscle, and cardiac muscle, vascular tissue including endothelial cells, liver tissue including hepatocytes, and nervous tissue including neurons. Methods of inducing differentiation of iPS cells into various differentiated cells types, including, but not limited to, cardiomyocytes, hematopoietic stem cells, bone cells such as, osteoclasts, hepatocytes, retinal cells, and neurons, are known in the art (Song at al., *Cell Res.,* 19(11):1233-42 (2009), Lamba at al, *PLoS One,* 5(1):e8763 (2010), Gai et al., *Cell Biol* 200933 (11):1184-93 (2009). Grigoriadis et al., *Blood,* 115(14): 2769-76 (2010)).

Stem cells including, but not limited to, isolated embryonic stem cells, hematopoietic stem cells, and induced pluripotent stem cells can be induced to differentiate by transient transfection with RNAs that induce differentiation. Additionally, or alternatively, cells can be re-differentiated by culturing the cells under cell type-specific conditions. For example, iPS cells can be maintained on CF-1 feeders and subsequently adapted to feeder-free conditions. iPS cells can be induced to form differentiated retinal cells by culturing the cells in the presences of noggin, Dkk-1, and IGF-1 (see for example Lamba et al, *PLoS One,* 5(1):e8763 (2010)).

In some embodiments, cells are re-programmed by transient transfection. For example, mRNA from transcription factors such as FoxP3 can be introduced into lymphocytes to increase the formation of regulatory T cells. FoxP3 (forkhead box P3) is a master regulator of development and function of regulatory T cells. Exemplary genomic, mRNA (cDNA), and protein sequences for FoxP3 are known in the art, see, for example Gene ID: 50943, which provides the mRNA (cDNA) sequences GENBANK® (sequence database) accession no. NM_014009.3 entitled *Homo sapiens* forkhead box P3 (FOXP3), transcript variant 1, mRNA; and GENBANK® (sequence database) accession no. Nm_001114377.1 entitled *Homo sapiens* forkhead box P3 (FOXP3), transcript variant 2, mRNA.

C. Therapeutic Applications

1. In Vivo Methods a. Pharmaceutical Compositions

Pharmaceutical compositions including nucleic acids and, optionally, polypeptides are provided. Pharmaceutical compositions can be for administration by parenteral (intramuscular, intraperitoneal, intravenous (1V) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

For example, in general, the compositions can be incorporated within or on microparticles. As used herein, microparticles include liposomes, virosomes, microspheres and microcapsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be produced by standard methods such as those reported by Kim, et al., Biochim. Biophys. Acta, 728, 339-348 (1983); Liu, D., et al., Biochim. Biophys. Acta, 1104, 95-101 (1992); and Lee, et al., Biochim. Biophys. Acta., 1103, 185-197 (1992); Wang, et at, Biochem., 28, 9508-9514 (1989)), incorporated herein by reference. The compositions can be encapsulated within liposomes when the molecules are present during the preparation of the microparticles. Briefly, the lipids of choice, dissolved in an organic solvent, are mixed and dried onto the bottom of a glass tube under vacuum. The lipid film is rehydrated using an aqueous buffered solution of the composition to be encapsulated, and the resulting hydrated lipid vesicles or liposomes encapsulating the material can then be washed by centrifugation and can be filtered and stored at 4° C. This method has been used to deliver nucleic acid molecules to the nucleus and cytoplasm of cells of the MOLT-3 leukemia cell line (Thierry, A. R. and Dritschilo, A., Nucl. Acids Res., 20: 5691-5698 (1992)). Alternatively the compositions can be incorporated within microparticles, or bound to the outside of the microparticles, either ionically or covalently.

Cationic liposomes or microcapsules are microparticles that are particularly useful for delivering negatively charged compounds such as nucleic acid-based compounds, which can bind ionically to the positively charged outer surface of these liposomes. Various cationic liposomes have previously been shown to be very effective at delivering nucleic acids or nucleic acid-protein complexes to cells both in vitro and in vivo, as reported by Feigner, P. L. et al., Proc. Natl. Acad. Sci. USA, 84: 7413-7417 (1987); Feigner, P. L., Advanced Drug Delivery Reviews, 5: 163-187 (1990); Clarenc, J. P. et al., Anti-Cancer Drug Design, 8: 81-94 (1993), incorporated herein by reference. Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl-]N,N,N-triethylammonium ("DOTMA," see Feigner, P. L. et al., Proc. Natl. Acad. Sci USA, 84, 7413-7417 (1987); Feigner, P. L. et al., Nature, 337, 387-388 (1989); Feigner, P. L., Advanced Drug Delivery Reviews, 5, 163-187 (1990)).

Nucleic acid can also be encapsulated by or coated on cationic liposomes which can be injected intravenously into a mammal. This system has been used to introduce DNA into the cells of multiple tissues of adult mice, including endothelium and bone marrow, where hematopoietic cells reside (see, for example, Zhu et al., Science, 261: 209-211 (1993)).

Liposomes containing nucleic acids can be administered systemically, for example, by intravenous or intraperitoneal administration, in an amount effective for delivery of the compositions to targeted cells. Other possible routes include trans-dermal or oral, when used in conjunction with appropriate microparticles. Generally, the total amount of the liposome-associated nucleic acid administered to an individual will be less than the amount of the unassociated nucleic acid that must be administered for the same desired or intended effect.

Compositions including various polymers such as the polylactic acid and polyglycolic acid copolymers, polyethylene, and polyorthoesters and the compositions can be delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Harwood Ltd., 1987), which can effect a sustained release of the therapeutic anti-hepatitis EGS compositions to the immediate area of the implant.

Various methods for nucleic acid delivery are described, for example, in Sambrook and Russell, Molecular Cloning: A Laboratory Manual, 3rd edition (2001); Current Protocols In Molecular Biology [(F. M. Ausubel, et al. eds., (1987)]; Plant Breeding: Principles and Prospects (Plant Breeding, Vol 1) M. D. Hayward, N. O. Bosemark, I. Romagosa; Chapman & Hall, (1993); Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)]. Such nucleic acid delivery systems include the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition, as discussed above. The nucleic acid delivery system can be provided to the cell either directly, such as by contacting it with the cell, or indirectly, such as through the action of any biological process. The nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration.

i. Formulations for Parenteral Administration

In a preferred embodiment, compositions disclosed herein, including those containing peptides and polypeptides, are administered in an aqueous solution, by parenteral injection. The formulation may also be in the form of a suspension or emulsion. In general, pharmaceutical compositions are provided including effective amounts of nucleic acid, polypeptides, or combinations thereof and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), antioxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

ii. Formulations for Topical Administration

The nucleic acids, polypeptides, or combinations thereof can be applied topically. Topical administration can include application to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.).

Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations can include penetration enhancers.

2. In Vitro and Ex Vivo Methods

The methods are particularly useful in the field of cell reprogramming and de-differentiation. In some embodiments, the methods are applied in the context of personalized therapy, for example, to generate iPS cells for introduction into a subject in need thereof. In vitro de-differentiation, re-differentiation, and/or reprogramming can be applied to a variety of different starting cell types and allows fast and safe generation of cells over a diverse range of de-differentiated or re-differentiated states. As used herein, in vitro de-differentiation, re-differentiation, and reprogramming includes de-differentiation, re-differentiation, and reprogramming of isolated cells ex vivo.

For example, target cells are first isolated from a donor using methods known in the art, contacted with one or more RNA's causing the cells to be de-differentiated, re-differentiated, or reprogrammed in vitro (ex vivo), and administered to a patient in need thereof. Sources or cells include, but are not limited to peripheral lymphocytes, fibroblasts, keratinocytes primary cell lines, or cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

In some embodiments the cells are contacted with one or more RNA that reprogram the cells to prevent expression of one or more antigens. For example, the RNA may be an interfering RNA that prevents expression of an mRNA encoding antigens such as CTLA-4 or PD-1.

This method can be used to prepare universal donor cells. RNAs used to alter the expression of allogenic antigens may be used alone or in combination with RNAs that result in de-differentiation of the target cell.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200 or 1000 orders of magnitude. Once target cells have been isolated, they may be propagated by growing in suitable medium according to established methods known in the art. Established cell lines may also be useful in for the methods. The cells can be stored frozen before transfection, if necessary.

Next the cells are contacted with the disclosed composition in vitro, for example using a transfection technique known in the art. De-differentiation, re-differentiation, and/or re-programming can be monitored, and the desired cell type can be selected for therapeutic administration.

iPS cells can be monitored and selected by identification of specific antigens, such as Nanog, Sox2, SSEA-3, SSEA-4, TRA-1-60, TRA-1-81, Oct 3/4 and alkaline phosphatase, and purified by different methods including magnetic column separation and flow cytometry.

Following de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of RNA-reprogrammed or dedifferentiated cells stored long-term, for later use. In one embodiment, fibroblasts, keratinocytes or hematopoietic stem cells are isolated from a patient and de-differentiation, and/or re-differentiated and/or reprogrammed in vitro to provide re-programmed cells for the patient.

The method can also be used to reprogram somatic cells wherein RNAs are introduced into cells in order to modulate their viability. For example, mRNA coding dominant-negative mutant p53 protein can temporarily block p53 function. This mRNA can be introduced into cells to protect them from p53-mediated apoptosis caused by metabolic disturbances during de-differentiation.

D. Diseases to be Treated

The methods can be used to generate cells which may be useful in the treatment or alleviation of one or more symptoms of a variety of diseases and disorders, including, but not limited to, neurodegenerative diseases such as Parkinson's, Alzheimer disease, and multiple sclerosis. The methods are also useful for organ regeneration, and for restoration or supplementation of the immune system. For example, cells at different stages of differentiation such as iPS cells, hematopoietic stem cells, multipotent cells or unipotent cells such as precursor cells, for example, epithelial precursor cells, and others can be administered intravenously or by local surgery. The methods can be used in combination with other conventional methods, such as a prescription medication regime, surgery, hormone therapy, chemotherapy and/or radiotherapy.

In some embodiments, reprogrammed cells are used for stimulating or enhancing an immune response. Stimulating an immune response in a host is desirable, for example, when the host suffers from a viral infection, bacterial infection, fungal, protozoa infection, or hyperproliferative condition such as cancer. Thus, one embodiment provides a method for treating infection by using the compositions to modulate an immune response against an infection.

Another embodiment provides methods and compositions for stimulating or enhancing an immune response in host for treating cancer by using the compositions to modulate an immune response against cancer cells. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

In some embodiments, cells are reprogrammed to modulate the immune response. For example, lymphocytes can be reprogrammed into regulatory T cells which can be administered to a patient in need thereof to increase or transfer immune tolerance, especially self-tolerance. The induction or administration of Foxp3 positive T cells may be useful in reducing autoimmune responses such graft rejection, and/or reducing, inhibiting or mitigating one or more symptoms of an autoimmune diseases or disorder such as diabetes, multiple sclerosis, asthma, inflammatory bowel disease, thyroiditis, renal disease, rheumatoid arthritis, or systemic lupus erythematosus.

IV. Kits

In one embodiment, a kit includes RNAs, cells, and a means for transfecting the RNA into the cells. The RNAs can be lyophilized or in solution. Kits may optionally include other materials such as cell culture reagents. In an alternative embodiment, a kit provides re-differentiated, dedifferentiated, or reprogrammed cells prepared according to the methods, and stored and/or shipped refrigerated or frozen for later use. Cells are typically stored in a solution maintaining viability. Kits containing cells should be stored or shipped using a method consistent with viability such as in a cooler containing dry ice so that cells are maintained below 4° C., and preferably below −20° C.

The kits optionally include one or more of the following: bioactive agents, media, excipients and one or more of: a syringe, a needle, thread, gauze, a bandage, a disinfectant, an antibiotic, a local anesthetic, an analgesic agent, surgical thread, scissors, a scalpel, a sterile fluid, and a sterile vessel. Components of the kit may be packaged individually and can be sterile. The kits are generally provided in a container, e.g., a plastic, cardboard, or metal container suitable for commercial sale. Any of the kits can include instructions for use.

The present invention will be further understood by the following non-limiting examples.

EXAMPLES

Materials and Methods

Cells and Cell Culture

BHK 21 cells were grown on DMEM (GIBCO) supplemented with 10% fetal bovine serum (FBS), supplemented with glutamine. Jurkat cells were maintained in RPMI medium supplemented with 10% fetal bovine serum (FBS) with glutamine. Human foreskin fibroblasts were obtained from Eugenie Cheng (laboratory of Haifan Lin, Yale). Cells were maintained in DMEM medium with 10% fetal bovine serum (FBS) with glutamine.

RNA Synthesis mRNA synthesis with T7 RNA polymerase has been described earlier (Rabinovich et al., *Hum. Gene Ther.,* 17(10):1027-1035 (2006)). Green fluorescent protein (GFP) mRNA constructs were based on the Pontellina plumata GFP sequence of plasmid PMAXGFP® (vector) (Amaxa Biosystems, Cologne, Germany), and were produced in vitro with T7 RNA polymerase. The NEO construct was made by insertion coding sequence of Tn5 aminoglycoside 3t-phosphotransferase.

NP, P, L, F, M and NH genes were obtained from pSV plasmid, a kind gift of Dr. V. Grdzelishvili (University of North Carolina). DNA templates were made by PCR. The reverse primer contained a stretch of 100 dT residues. mRNA synthesis was performed with a "MMESSAGE MMACHINE® (RNA transcription) T7 ULTRA" kit or MEGASCRIPT® (invitro transcription kit) (Ambion, Austin, Tex.), using the procedure recommended by the manufacturer. In some cases the product was additionally treated with *Escherichia coli* poly(A) polymerase (Ambion). The final product was treated with DNase I (Ambion) and purified with an Ambion MEGACLEAR™ (transcription clean-up kit) or by LiCl precipitation. RNA quality was verified by agarose gel electrophoresis, and RNA was stored at −80° C.

Transfection

Transfection was performed by lipofection with LIPOFECTINS® (transfection reagent) and LIPOFECTAMINE® (transfection reagent) INVITROGEN™, using standard procedures, or by use of nucleoporation. All procedures were performed as directed by the manufacturers. PMAXGFP® (vector) plasmid DNA (Amaxa Biosystems) was used as the DNA control. The efficiency of transfection was determined by fluorescent microscopy or by flow cytometry. Transfectants were further analyzed at different time intervals until GFP could no longer be detected. Cell viability was determine by trypan blue dye exclusion.

Nucleoporation was performed with an Amaxa NUCLEOFECTOR™ II (transfection device) (Amaxa Biosystems) in accordance with the manufacturer's recommendations.

Flow Cytometry

FACS assay of cell subpopulations was performed at the Yale Cancer Center Flow Cytometry Shared Resource (New Haven, Conn.), using a FACSCalibur flow cytometer (BD Biosciences Immunocytometry Systems, San Jose, Calif.) equipped with a 488-nm laser and the standard filter setup. Fluorescence signals were collected on a logarithmic scale. At least 10,000 cells were investigated for each sample. Analysis of data was performed with FlowJo software (Tree Star, Ashland, Oreg.). Expression efficiency was calculated as the difference between the geometric mean of fluorescence of the transfectants and control (mock-transfected) cells. Cell sorting was done with the Reflection iCyt system.

Fluorescent Microscopy

Fluorescent microscopy was used to evaluate GFP expression in growing cell cultures. The images of three randomly selected fields per each well were analyzed with a Nikon Eclipse TS100 inverted microscope by using bright-field and phase-contrast microscopy. At least 200 cells for each condition were analyzed, and the data were obtained from a minimum of three independent samples.

Electrophoresis

DNA samples were run in 1% agarose in Tris-acetate buffer (Sigma), 2 V/cm. RNA samples were run in 1% agarose in morpholinepropanesulfonic acid (MOPS)-formaldehyde buffer (Ambion), 2 V/cm, using an RNA Millennium marker (Invitrogen) as size standard.

RT PCR

RT-PCT was performed by standard procedure with use of primers for GFP and GAP genes.

Results

Example 1: GYP RNA can be "Rescued" from a "Genomic" RNA Template Unit (rTeUn)

Materials and Methods

In this assay, illustrated in FIG. 1, NP, P and L containing plasmids were replaced with "supplemental" NP, P and L mRNAs. Each mRNA contained ARCA Cap, 5'UTR, coding sequence, 3'UTR and polyA tail (~400 Nu). $10^5$ cells were plated in a 24 well plate, then the four RNAs were applied to the well: GFP TeUn, NP, L and L were introduced in BHK21 cells in different combinations.

A PCR-produced DNA template contained as "genomic" sequence (5'-3' direction) the following elements of Sendai virus (SeV) and GFP: T7 promotor, SeV leader, SeV promotor region of N gene, GFP (700 Nu), SeV terminator region of L gene, SeV trailer, hammerhead ribozyme, T7 terminator, PolyA tail.

The sequence of DNA template:

```
                                        (SEQ ID NO: 18)
taatacgactcactataggaccaaacaagagaaaaaacatgtatggaata

tataatgaagtcagacaggattttagggtcaaagtatccaccctgaggag

caggttccagaccctttgctttgctgccaaagttcacgatgcccgccatg

aagatcgagtgccgcatcaccggcaccctgaacggcgtggagttcgagct

ggtgggcggcggagagggcacccccgagcagggccgcatgaccaacaaga

tgaagagcaccaagggcgccctgaccttcagcccctacctgctgagccac

gtgatgggctacggcttctaccacttcggcacctaccccagcggctacga

gaaccccttcctgcacgccatcaacaacggcggctacaccaacacccgca

tcgagaagtacgaggacggcggcgtgctgcacgtgagcttcagctaccgc

tacgaggccggccgcgtgatcggcgacttcaaggtggtgggcaccggctt

ccccgaggacagcgtgatcttcaccgacaagatcatccgcagcaacgcca

ccgtggagcacctgcaccccatgggcgataacgtgctggtgggcagcttc

gcccgcaccttcagcctgcgcgacggcggctactacagcttcgtggtgga

cagccacatgcacttcaagagcgccatccaccccagcatcctgcagaacg

gggccccatgttcgccttccgccgcgtggaggagctgcacagcaacacc

gagctgggcatcgtggagtaccagcacgccttcaagaccccgatcgcatt

cgccagatctcgagctcgataataattagtccctatcgtgcagaacgatc

gaagctccgcggtacctggaagtcttggacttatccatatgacaatagta

agaaaaacttacaagaagacaagaaaatttaaaagaataaatatctctta

aactcttgtctggtggccggcatggtcccagcctcctcgctggcgccggc

tgggcaacattccgaggggaccgtcccctcggtaatggcgaatgggacgg

atccctgcagctcgagaggcctaattaattaagtcgacgatccggctgct

aacaaagcccgaaaggaagctgagttggctgctgccaccgctgagcaata

actagcataaccccttggggcctctaaacgggtcttgaggggttttttgc

tgaaaggaggaactatatccggatcgaga-PolyA(100)
```

Synthetic GFP mRNA was made on PCR DNA templates. The RNA contained ARCA Cap, 5'UTR, GFP coding sequence, 3'UTR and a polyA tail (~400 Nu). This mRNA was introduced into different eukaryotic cells, including Jurkat cells, fibroblasts, and BHK21 cells. The GFP mRNA content was evaluated by RT-PCR and GFP protein content was evaluated by flow cytometry.

Results

Figures 2A, 2B:
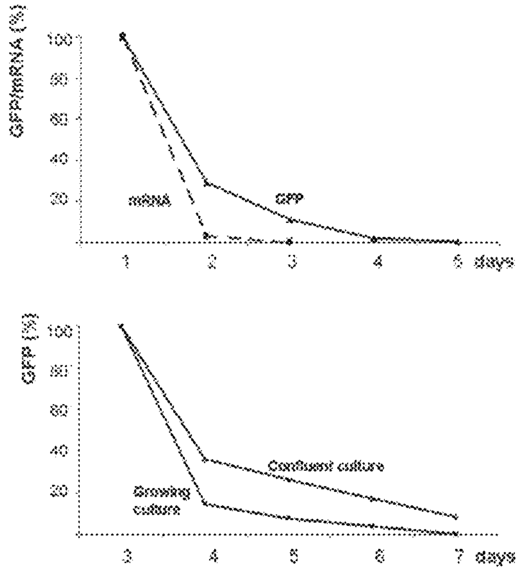
FIG. 2A is a line graph showing the duration of GFP expression (GFP/mRNA (%)) over time (days) in BHK21 cells for GFP mRNA (-■-) detected by RT-PCT or GFP protein (-▲-) detected by flow cytometry.
FIG. 2B is a line graph showing the duration of GFP expression (GFP (%)) over time (days) in growing and confluent human foreskin (HF) cells.

This RNA template unit can be rescued by a standard Sendai "reverse genetic" approach, using cotransfection with plasmids coding viral NP, P and L proteins placed under T7 promoters, in eukaryotic cells expressing T7 polymerase. GFP expression in BHK 21 cells transfected with GFP mRNA or rTeUn GFP RNA together with 3 supplemental mRNAs (NP, P and L) was increased. See FIGS. 2A, 2B. Cells transfected with GFP mRNA lost GFP within the first week of growth. Cells transfected with GFP rTeUn kept substantial fluorescence during the duration of the experiment.

The optimal mix included 0.4 μg GFP Te Un, 0.6 μg NP mRNA, 0.2 μP mRNA and 0.1 μg L mRNA. After 24, 48 h and 72h clones with "rescued" GFP TeUn complexes were determined by green fluorescence. 0.1-2% of the cell population became fluorescent, and the ratio GFP+/GFP− cells increased during the two days after transfection.

Example 2: GFP RNA can be "Rescued" from an "Anti-Genomic" RNA Template Unit (rTeUn)

Materials and Methods

The anti-genomic GFP rTeUn includes the same elements as genomic rTeUn, but in inverse orientation. It contains (3'-5' direction): T7 promotor SeV trailer, SeV terminator region of L gene, GFP, SeV promoter region of N gene, SeV leader, hammerhead ribozyme, T7 terminator, PolyA tail (100 Nu). The sequence of DNA template:

```
                                        (SEQ ID NO: 19)
taatacgactcactataggaccagacaagagtttaagagatatttattct

tttaaattttcttgtcttcttgtaagtttttcttactattgtcatatgga

taagtccaagacttccaggtaccgcggagcttcgatcgttctgcacgata

gggactaaccattattatcgagctcgagatctggcgaatgcgatcggggt

cttgaaggcgtgctggtactccacgatgcccagctcggtgttgctgtgca

gctcctccacgcggcggaaggcgaacatggggcccccgttctgcaggatg

ctggggtggatggcgctcttgaagtgcatgtggctgtccaccacgaagct

gtagtagccgccgtcgcgcaggctgaaggtgcgggcgaagctgcccacca

gcacgttatcgcccatggggtgcaggtgctccacggtggcgttgctgcgg

atgatcttgtcggtgaagatcacgctgtcctcggggaagccggtgcccac

caccttgaagtcgccgatcacgcggccggcctcgtagcggtagctgaagc

tcacgtgcagcacgccgccgtcctcgtacttctcgatgcgggtgttggtg

tagccgccgttgttgatggcgtgcaggaaggggttctcgtagccgctggg

gtaggtgccgaagtggtagaagccgtagcccatcacgtggctcagcaggt

aggggctgaaggtcagggcgcccttggtgctcttcatcttgttggtcatg

cggccctgctcgggggtgccctctccgccgcccaccagctcgaactccac

gccgttcagggtgccggtgatgcggcactcgatcttcatggcgggcatcg

tgaactttggcagcaaagcaaagggtctggaacctgctcctcagggtgga
```

-continued

```
tactttgaccctaaaatcctgtctgacttcattatatattccatacatgt

tttttctcttgtttggtggccggcatggtcccagcctcctcgctggcgcc

ggctgggcaacattccgaggggaccgtcccctcggtaatggcgaatggga

cggatccctgcagctcgagaggcctaattaattaagtcgacgatccggct

gctaacaaagcccgaaaggaagctgagttggctgctgccaccgctgagca

ataactagcataaccccttggggcctctaaacgggtcttgaggggttttt

tg-PolyA (100)
```

This construct was introduced into cells together with supplemental ("SU") NP, P, and L mRNA, under the same conditions as genomic GFP rTeUn.

Results

The kinetics of rTeUn rescue was similar, the ratio GFP+/GFP− cells increased during two days after transfection, however the efficiency of the rescue was higher: 1-5% of the cells became fluorescent 2 days after transfection.

GFP+ cell were sorted and further propagated to determine the duration of rTeUn GFP expression in comparison to "conventional" GFP mRNA. In exponentially growing culture, fluorescent cells disappeared 4 days after GFP mRNA transfection. In contrast, the cells containing GFP rTeUn construct could maintain substantial levels of fluorescence up to 2 weeks after transfection.

Example 3: Subsequent Transfection with Additional NP, P and L mRNAs Results in Reactivation of rTeUn In clones containing rTeUn RNA, nucleoprotein complexes can be reactivated and visualized by reoccurrence of GFP rTeUn expression via additional transfection with NP, P and L mRNAs.

Materials and Methods

BHK21 were transfected with GFP mRNA or rTeUn GFP RNA together with 3 supplemental mRNAs (NP, P and L).

Results

Cells transfected with GFP mRNA lost GFP within the first week of growth. Cells transfected with GFP rTeUn kept substantial fluorescence during the duration of the experiment.

Figures 3A, 3B:
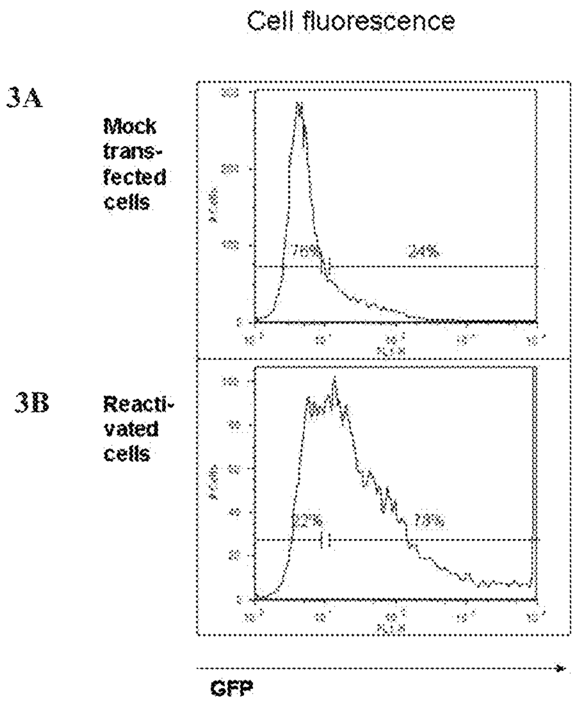
FIGS. 3A-3B are pairs of one parameter histogram showing the number of GFP positive (FL1-H detection, log scale) mock-transfected cells (3A) compared to cells transfected with anti-genomic rTeUn RNA encoding GFP and reactivated with N, L, and NP (3B). Fluorescence was measured by flow cytometry two days after reactivation (day 11).

Nine days after transfection with control (GFP mRNA) and anti-genomic GFP rTeUn, cells were retransfected with supplemental mRNAs: N, P and L exactly as was done during first transfection with GFP rTeUn. This additional transfection had no effect on control cells initially transfected with GFP mRNA. However, 75-80% of the fluorescent cells obtained with GFP rTeUn, could be "reactivated" with supplemental mRNAs to the level of fluorescence observed after the first transfection (FIGS. 3A and 3B).

Figures 4A, 4B:
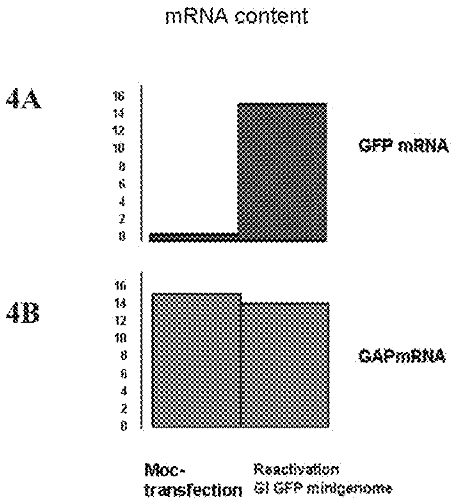
FIG. 4A-4B is a pair of bar graphs showing the relative levels of GFP mRNA (4A) or control GAPmRNA (4B) for mock-transfected cells ("moc-transfection") compared to cells transfected with anti-genomic rTeUn RNA encoding GFP and reactivated with N, L, and NP ("Reactivation GI GFP minigenome") (day 11).

FIG. 4A shows that only cells transfected with GFP rTeUn, but not with GFP mRNA, were able to reactivate GFP expression. Bright fluorescence in occasional cells transfected with GFP mRNA was associated with dead or growth arrested cells. Bright fluorescent GFP rTeUn+ cells showed conventional diffuse staining and continued to propagate. The duration of GFP expression in "reactivated" GFP rTeUn clones was the same as after the first transfection: the cell fluorescence slowly decreased during 2 weeks after reactivation.

Figures 5A, 5B:
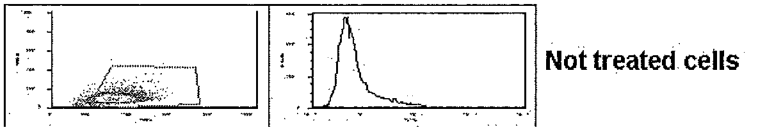
FIGS. 5A-5N are a series of histograms showing the results of flow cytometry on GFP rTeUn+ BHK21 cells propagated after the rescue procedure and on clay 9 transfected with different combinations of supplemental mRNAs: NP, P, or L as labeled. The left column (A, C, E, G, I, K, M) represents gated cell populations. The right column (B, D, F, H, J, L, N) shows cell fluorescence (X axis) and their number (Y axis). Each diagram in the right column is a superposition of a certain sample and an untreated control.
Figures 5C, 5D:
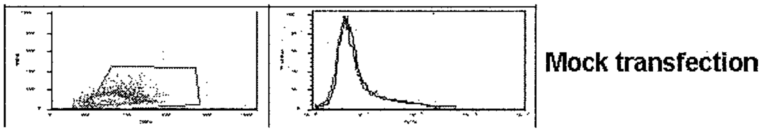
FIGS. 5C,D, mock transfected cells; Figures E,F, N treated cells; Figures G,H, L treated cells; Figures I,J, P treated cells; Figures K,L, LP treated cells; and Figures M,N, NLP treated cells.
Figures 5E, 5F:
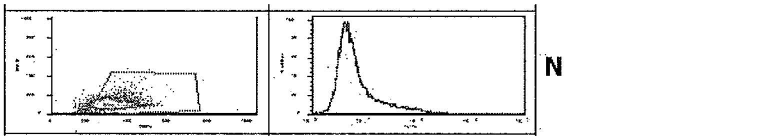
Figures 5G, 5H:
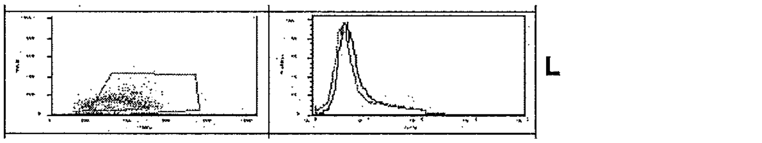
Figures 5I, 5J:
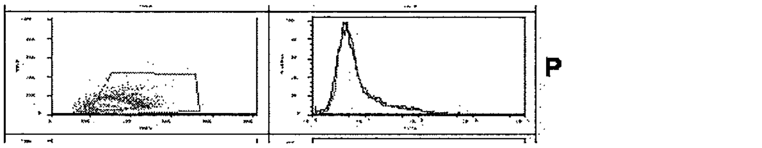
Figures 5K, 5L:
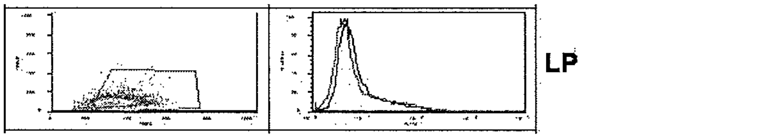
Figures 5M, 5N:
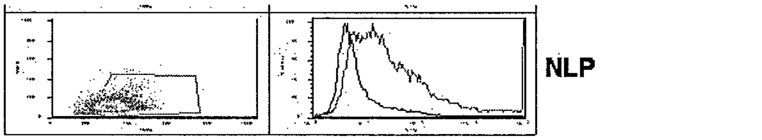

Additional results are shown in FIGS. 5A-5N. On day 9 after GFP rTeNu rescue, BHK21 cells were reactivated with 3 supplemental mRNAs or treated with LIPOFECTAMINE® (transfection reagent) without mRNAs (mock transfection). Cell fluorescence was analyzed by flow cytometry, mRNA content was determined by RT PCR. The reactivation of GFP mRNA transcription in the GFP rTeUn+ cell population was accompanied by an increase of GFP+/GFP− ratio and cell fluorescence intensity. On day 2 after reactivation, the proportion of fluorescent cells in culture increased from 24% to 78%, which was accompanied by a dramatic increase in GFP mRNA transcription and accumulation of GFP in cells. Cells containing GFP TeUn were also transfected with different combinations of supplemental mRNAs. Only transfection with all three mRNAs (NP, P and L) reactivated GFP rTeUn expression (FIG. 4).

Example 4: rTeUn Transfected Cells can be Repeatedly Reactivated

Materials and Methods

On day 0, BHK21 cells were transfected with GFP mRNA or GFP rTeNu RNA together with supplemental mRNA (NP, P and L) as in Example 24, and GFP+ cells were sorted on day 3 (100% fluorescence). Then the growing cells were repeatedly transfected with 3 supplemental mRNAs on days 9, 17 and 25.

Results

As shown in FIG. 6, cells could be repeatedly reactivated. Approximately 20% of cells loaded with GFP rTeUn were not reactivatable, probably because of GDP rTeUn spontaneous elimination. Although fluorescence intensity of individual cells was similar after each reactivation, the continuous loss of rTeUn in the population resulted in decreasing of total cell fluorescence. By repeated "reactivation" with supplemental mRNAs, transcriptionally active rTeUn complexes can persist for at least 35 days, in growing cell culture.

Example 5: rTeUn RNAs can Include the Sequences of Multiple Genes

Materials and Methods rTeUn RNAs can include the sequence of multiple genes. These constructs can be made as "multi-genic" structures (a rTeUn encoding multiple proteins of interest) or comprise a mixture of different rTeUns molecules, each coding single proteins. Because of the highly efficient method of delivery, both methods can be used for gene transfer. Multi genic structures may contain fused or separate coding sequences. Separation can be achieved by introduction of SeV inergenic sequences, such as sequence that separate genes NP and P.

The sequence of DNA template:

```
(SEQ ID NO: 20)
TAATACGACTCACTATAGGACCAGACAAGAGTTTAAGAGATATTTATTCT

TTTAAATTTT

CTTGTCTTCTTGTAAGTTTTTCTTACTATTGTCATATGGATAAGTCCAAG

ACTTCCAGGT

ACCGCGGAGCTTCGATCGTTCTGCACGATAGGGACTAACCATTATTAGAA

GAACTCGTCA

AGAAGGCGATAGAAGGCGATGCGCTGCGAATCGGGAGCGGCGATACCGTA

AAGCACGAGG

AAGCGGTCAGCCCATTCGCCGCCAAGCTCTTCAGCAATATCACGGGTAGC
```

-continued

CAACGCTATG

TCCTGATAGCGGTCCGCCACACCCAGCCGGCCACAGTCGATGAATCCAGA

AAAGCGGCCA

TTTTCCACCATGATATTCGGCAAGCAGGCATCGCCATGGGTCACGACGAG

ATCCTCGCCG

TCGGGCATGCGCGCCTTGAGCCTGGCGAACAGTTCGGCTGGCGCGAGCCC

CTGATGCTCT

TCGTCCAGATCATCCTGATCGACAAGACCGGCTTCCATCCGAGTACGTGC

TCGCTCGATG

CGATGTTTCGCTTGGTGGTCGAATGGGCAGGTAGCCGGATCAAGCGTATG

CAGCCGCCGC

ATTGCATCAGCCATGATGGATACTTTCTCGGCAGGAGCAAGGTGAGATGA

CAGGAGATCC

TGCCCCGGCACTTCGCCCAATAGCAGCCAGTCCCTTCCCGCTTCAGTGAC

AACGTCGAGC

ACAGCTGCGCAAGGAACGCCCGTCGTGGCCAGCCACGATAGCCGCGCTGC

CTCGTCCTGC

AGTTCATTCAGGGCACCGGACAGGTCGGTCTTGACAAAAAGAACCGGGCG

CCCCTGCGCT

GACAGCCGGAACACGGCGGCATCAGAGCAGCCGATTGTCTGTTGTGCCCA

GTCATAGCCG

AATAGCCTCTCCACCCAAGCGGCCGGAGAACCTGCGTGCAATCCATCTTG

TTCAATAACC

ATGGTTGTGGCGTGATGGTGATGGTGATGTCGAGCTCGAGATCTGGCGAA

TGCGATCGGG

GTCTTGAAGGCGTGCTGGTACTCCACGATGCCCAGCTCGGTGTTGCTGTG

CAGCTCCTCC

ACGCGGCGGAAGGCGAACATGGGGCCCCCGTTCTGCAGGATGCTGGGGTG

GATGGCGCTC

TTGAAGTGCATGTGGCTGTCCACCACGAAGCTGTAGTAGCCGCCGTCGCG

CAGGCTGAAG

GTGCGGGCGAAGCTGCCCACCAGCACGTTATCGCCCATGGGGTGCAGGTG

CTCCACGGTG

GCGTTGCTGCGGATGATCTTGTCGGTGAAGATCACGCTGTCCTCGGGGAA

GCCGGTGCCC

ACCACCTTGAAGTCGCCGATCACGCGGCCGGCCTCGTAGCGGTAGCTGAA

GCTCACGTGC

AGCACGCCGCCGTCCTCGTACTTCTCGATGCGGGTGTTGGTGTAGCCGCC

GTTGTTGATG

GCGTGCAGGAAGGGGTTCTCGTAGCCGCTGGGGTAGGTGCCGAAGTGGTA

GAAGCCGTAG

-continued

CCCATCACGTGGCTCAGCAGGTAGGGGCTGAAGGTCAGGGCGCCCTTGGT

GCTCTTCATC

TTGTTGGTCATGCGGCCCTGCTCGGGGGTGCCCTCTCCGCCGCCCACCAG

CTCGAACTCC

ACGCCGTTCAGGGTGCCGGTGATGCGGCACTCGATCTTCATGGCGGGCAT

CGTGAACTTT

GGCAGCAAAGCAAAGGGTCTGGAACCTGCTCCTCAGGGTGGATACTTTGA

CCCTAAAATC

CTGTCTGACTTCATTATATATTCCATACATGTTTTTCTCTTGTTTGGTG

GCCGGCATGG

TCCCAGCCTCCTCGCTGGCGCCGGCTGGGCAACATTCCGAGGGGACCGTC

CCCTCGGTAA

TGGCGAATGGGACGGATCCCTGCAGCTCGAGAGGCCTAATTAATTAAGTC

GACGATCCGG

CTGCTAACAAAGCCCGAAAGGAAGCTGAGTTGGCTGCTGCCACCGCTGAG

CAATAACTAG

CATAACCCCTTGGGGCCTCTAAACGGGTCTTGAGGGGTTTTTTG

PolyA (100)

A GFP-NEO rTeUnI RNA has a structure similar to rTeUn from Example 2.

As a coding sequence it contains fused GFP (700 Nu) and Neo (G418R+, 900 Nu) sequence. The RNA construct was introduced into BHK 21 cells in the presence of NP, P and L mRNAs.

Results

GFP positive clones were obtained with similar efficiency to GFP rTeUn RNA.

Example 6: rTeUn RNAs Can be Packaged in Virus-Like Particles

Materials and Methods rTeUn RNAs that include sequences of desirable genes or encode antigens can be used together with supplemental mRNAs NP, P and L and packaging proteins such as F, M, NH to produce viral-like particles containing rTeUn nucleoprotein complex. Such harvested particles can subsequently be used to transfer rTeUn nucleoprotein with high efficiency in various human and animal cells. A packaging system can be obtained from a cell line where rTeUn RNA has been rescued with supplemental mRNAs by adding packaging agents as describe above (M, F, NH proteins or their encoding mRNAs). Packaging agents can be introduced by mRNA mediated transfection or by direct introduction of M, F, NH proteins as it was described for supplemental mRNAs.

BHK 21 cells were transfected with antisense GFP-NEO rTeUn RNA together with mRNAs coding NP, P, L, M, F, NH genes or just NP, P, and L mRNA (control). The following day cell medium was replaced with new growth medium. Cell medium was collected 3 days after transfection (3 day Supernatant and 3 day Supernatant control) centrifuged to remove cell debris and frozen. The 3 day Supernatant and 3 day Supernatant control then were analyzed for the presence of viral-like particles containing GFP-Neo rTeUn.

A new portion of BHK cells was transfected with NP, P and L mRNAs (day 1). The following day (day 2) cells were washed from the transfection medium and covered with 3 day Supernatant or 3 day Supernatant control.

Results

At day 5 fluorescent colonies were detected in the cells treated with 3 day supernatant, but not in the 3 day supernatant control. The titer of the particles in different experiments varied from $10^2$ to $5\times10^3$ per ml prior to concentrating the viral particles.

The production of viral-like particles can be further increased by optimization of the concentration of SU viral mRNAs. Alternatively, specially designed "packaging cells" stably transduced/transfected to produce (or containing) viral M, F and NH genes can be used. In both cases it is possible to accumulate a sufficient number of viral-like particles able to efficiently introduce a rTeUn RNA complex into a population of recipient cells.

We claim:

1. A DNA-free composition comprising
(i) a non-integrating ribonucleic acid (RNA) recombinant template unit (rTeUn) comprising negative-strand virus regulatory sequences operably linked to a sequence encoding one or more genes of interest, wherein the rTeUn does not contain any intact viral genes, and wherein the RNA rTeUn RNA is prepared by in vitro transcription of a DNA template comprising the sequence of SEQ ID NO:_1 operably linked to the sequence of the one or more genes of interest operably linked to the sequence of SEQ ID NO: 2, and
(ii) mRNA encoding one or more proteins necessary to control transcription of the rTeUn in a host cell.

2. The composition of claim 1, wherein the one or more genes of interest encode non-translated functional RNA.

3. The composition of claim 2, wherein non-translated functional RNA is selected from the grouping consisting of siRNA, miRNA, aptamers, ribozymes, triplex forming molecules, RNAi, and external guide sequences.

4. The composition of claim 1, wherein the one or more genes of interest encode a polypeptide selected from the group consisting of receptors, anti-apoptotic factors, transcription factors, pro-apoptotic factors, and cytokines.

5. The composition of claim 1, wherein the one or more genes of interest encode a polypeptide selected from the group consisting of selectable markers and reporter genes.

6. The composition of claim 4, wherein the transcription factor is selected from the group consisting of OCT4, SOX2, NANOG, LIN28, SOX2, KLF4, c-MYC, and combinations thereof.

7. The composition of claim 1 comprising mRNAs encoding all proteins sufficient to control transcription of the rTeUn in the host cell.

8. The composition of claim 7 comprising mRNAs encoding all proteins sufficient to control replication of the rTeUn in the host cell.

9. The composition of claim 8, wherein the mRNAs comprise a natural, synthetic or modified 5'_Cap, 5' untranslated region (UTR), 3'UTR and a polyA tail.

10. The composition of claim 8 comprising mRNAs encoding all proteins sufficient to control formation of virus-like particles containing the rTeUn.

11. The composition of claim 10, wherein the proteins sufficient to control formation of virus-like particles comprise F, HN, and M of Sendai virus.

12. The composition of claim 1 comprising mRNAs encoding the nucleoprotein (NP) of Sendai virus (SeV), phosphoprotein (P) of SeV, large protein (L) of SeV, or a combination thereof.

13. The composition of claim 1 comprising mRNAs encoding nucleoprotein (NP) of SeV, phosphoprotein (P) of SeV, and large protein (L) of SeV.

14. A method of transient gene expression in a cell comprising contacting the cell with an effective amount of the composition of claim 1 under conditions suitable to introduce the reTeUn and mRNA into the cell.

15. The method of claim 14, wherein the rTeUn and mRNA are introduced into the cell by lipofection, by electroporation, by nucleoporation, by hydrodynamic shock, or in nanoparticles.

16. The method of claim 14, wherein the rTeUn is introduced into the cell by incorporating the rTeUn into viral-like particles coated by a virus protein to form pseudoviral particles, and infecting cells with the pseudoviral particles.

17. The method of claim 15, wherein the rTeUn and mRNA are introduced into the cell by lipofection or by nucleoporation.

18. The method of claim 14, wherein the mRNA is reintroduced into the cell one or more times in an effective amount to increase efficiency of rTeUn expression in the cell, duration of rTeUn expression in the cell, or a combination thereof.

19. A method of expressing a tumor antigen in a lymphocyte comprising contacting a lymphocyte in vitro with the composition of claim 1 under conditions suitable to introduce the rTeUn and mRNA into the lymphocyte, wherein the one or more genes of interest encode a tumor antigen.

20. A method of de-differentiating a somatic cell to form an induced pluripotent stem (iPS) cell comprising contacting a somatic cell in vitro with the composition of claim 1 under conditions suitable to introduce the rTeUn and mRNA into the somatic cell, wherein the one or more genes of interest encode OCT4, SOX2, c-MYC and KLF4.

21. A method of de-differentiating a somatic cell to form an iPS cell comprising contacting a somatic cell in vitro with the composition of claim 1 under conditions suitable to introduce the rTeUn and mRNA into the somatic cell, wherein the one or more genes of interest encode OCT4, SOX2, NANOG and LIN28.

22. The method of claim 14, wherein the contacting occurs ex vivo.

* * * * *

SEQUENCE LISTING

```
<160> NUMBER OF SEQ ID NOS: 20

<210> SEQ ID NO 1
<211> LENGTH: 119
<212> TYPE: DNA
<213> ORGANISM: Artificial Sequence
<220> FEATURE:
<223> OTHER INFORMATION: Synthetic regulatory requence of a Recombinant
      template unit

<400> SEQUENCE: 1

accaaacaag agaaaaaaca tgtatggaat atataatgaa gtcagacagg attttagggt     60

caaagtatcc accctgagga gcaggttcca gaccctttgc tttgctgcca aagttcacg     119


<210> SEQ ID NO 2
<211> LENGTH: 510
<212> TYPE: DNA
<213> ORGANISM: Artificial Sequence
<220> FEATURE:
<223> OTHER INFORMATION: Synthetic regulatory requence of a Recombinant
      template unit

<400> SEQUENCE: 2

taataattag tccctatcgt gcagaacgat cgaagctccg cggtacctgg aagtcttgga     60

cttatccata tgacaatagt aagaaaaact tacaagaaga caagaaaatt taaaagaata    120

aatatctctt aaactcttgt ctggtggccg gcatggtccc agcctcctcg ctggcgccgg    180

ctgggcaaca ttccgagggg accgtcccct cggtaatggc gaatgggacg gatccctgca    240

gctcgagagg cctaattaat taagtcgacg atccggctgc taacaaagcc cgaaaggaag    300

ctgagttggc tgctgccacc gctgagcaat aactagcata accccttggg gcctctaaac    360

gggtcttgag gggttttttg ctgaaaggag gaactatatc cggatcgaga aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa                                     510


<210> SEQ ID NO 3
<211> LENGTH: 145
<212> TYPE: DNA
<213> ORGANISM: Artificial Sequence
<220> FEATURE:
<223> OTHER INFORMATION: Synthetic antigenomic sequence of  regulatory
      requence of a Recombinant template unit

<400> SEQUENCE: 3

accagacaag agtttaagag atatttattc ttttaaattt tcttgtcttc ttgtaagttt     60

ttcttactat tgtcatatgg ataagtccaa gacttccagg taccgcggag cttcgatcgt    120

tctgcacgat agggactaat tatta                                          145
```

```
<210> SEQ ID NO 4
<211> LENGTH: 538
<212> TYPE: DNA
<213> ORGANISM: Artificial Sequence
<220> FEATURE:
<223> OTHER INFORMATION: Synthetic antigenomic sequence of  regulatory
      requence of a Recombinant template unit

<400> SEQUENCE: 4
cgtgaacttt ggcagcaaag caaagggtct ggaacctgct cctcagggtg gatactttga     60
ccctaaaatc ctgtctgact tcattatata ttccatacat gtttttctc ttgtttggtg    120 gccggcatgg tcccagcctc ctcgctggcg ccggctgggc aacattccga ggggaccgtc    180
ccctcggtaa tggcgaatgg gacggatccc tgcagctcga gaggcctaat taattaagtc    240
gacgatccgg ctgctaacaa agcccgaaag gaagctgagt tggctgctgc caccgctgag    300
caataactag cataacccct tggggcctct aaacgggtct tgaggggttt tttgggccgg    360
catggtccca gcctcctcgc tggcgccggc tgggcaacat tccgagggga ccgtcccctc    420
ggtaatggcg aatgggacaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaa      538

<210> SEQ ID NO 5
<211> LENGTH: 524
<212> TYPE: PRT
<213> ORGANISM: Sendai virus

<400> SEQUENCE: 5

Met Ala Gly Leu Leu Ser Thr Phe Asp Thr Phe Ser Ser Arg Arg Ser
1               5                   10                  15

Glu Ser Ile Asn Lys Ser Gly Gly Gly Ala Val Ile Pro Gly Gln Arg
            20                  25                  30

Ser Thr Val Ser Val Phe Val Leu Gly Pro Ser Val Thr Asp Asp Ala
        35                  40                  45

Asp Lys Leu Phe Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
            100                 105                 110

Thr Lys Thr Asp Gly Phe Ile Val Lys Thr Arg Asp Met Glu Tyr Glu
        115                 120                 125

Arg Thr Thr Glu Trp Leu Phe Gly Pro Met Val Asn Lys Ser Pro Leu
    130                 135                 140

Phe Gln Gly Gln Arg Val Ala Ala Asp Pro Asp Thr Leu Leu Gln Thr
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Gly Ala
        195                 200                 205

Leu Val Phe Thr Gly Glu Thr Val Glu Gly Ile Gly Ser Val Met Arg
    210                 215                 220
```

-continued

Ser Gln Gln Ser Leu Val Ser Leu Met Val Glu Thr Leu Val Thr Met
225 230 235 240

Asn Thr Ala Arg Ser Asp Leu Thr Thr Leu Glu Lys Asn Ile Gln Ile
245 250 255

Val Gly Asn Tyr Ile Arg Asp Ala Gly Leu Ala Ser Phe Met Asn Thr
260 265 270

Ile Lys Tyr Gly Val Glu Thr Lys Met Ala Ala Leu Thr Leu Ser Asn
275 280 285

Leu Arg Pro Asp Ile Asn Lys Leu Arg Ser Leu Ile Asp Thr Tyr Leu
290 295 300

Ser Lys Gly Pro Arg Ala Pro Phe Ile Cys Ile Leu Lys Asp Pro Val
305 310 315 320

His Gly Glu Phe Ala Pro Gly Asn Tyr Pro Ala Leu Trp Ser Tyr Ala
325 330 335

Met Gly Val Ala Val Val Gln Asn Lys Ala Met Gln Gln Tyr Val Thr
340 345 350

Gly Gly Thr Tyr Leu Asp Met Glu Met Phe Leu Leu Gly Gln Ala Val
355 360 365

Ala Lys Asp Ala Glu Ser Lys Ile Ser Ser Ala Leu Glu Asp Glu Leu
370 375 380

Gly Val Thr Asp Thr Ala Lys Glu Arg Leu Arg His His Leu Ala Asn
385 390 395 400

Leu Ser Gly Gly Asp Gly Ala Tyr His Glu Pro Thr Gly Gly Gly Ala
405 410 415

Ile Glu Val Ala Leu Asp Asn Ala Asp Ile Asp Leu Glu Thr Glu Ala
420 425 430

His Ala Asp Gln Asp Ala Arg Gly Trp Gly Gly Glu Ser Gly Glu Arg
435 440 445

Trp Ala Arg Gln Val Ser Gly Gly His Phe Val Thr Leu His Gly Ala
450 455 460

Glu Arg Leu Glu Glu Glu Thr Asn Asp Glu Asp Val Ser Asp Ile Glu
465 470 475 480

Arg Arg Ile Ala Met Arg Leu Ala Glu Arg Arg Gln Glu Asp Ser Ala
485 490 495

Thr His Gly Asp Glu Gly Arg Asn Asn Gly Val Asp His Asp Glu Asp
500 505 510

Asp Asp Ala Ala Ala Val Ala Gly Ile Gly Gly Ile
515 520

<210> SEQ ID NO 6
<211> LENGTH: 568
<212> TYPE: PRT
<213> ORGANISM: Sendai virus

<400> SEQUENCE: 6

Met Asp Gln Asp Ala Phe Ile Leu Lys Glu Asp Ser Glu Val Glu Arg
1 5 10 15

Glu Ala Pro Gly Gly Arg Glu Ser Leu Ser Asp Val Ile Gly Phe Leu
20 25 30

Asp Ala Val Leu Ser Ser Glu Pro Thr Asp Ile Gly Gly Asp Arg Ser
35 40 45

Trp Leu His Asn Thr Ile Asn Thr Pro Gln Gly Pro Gly Ser Ala His
50 55 60

Arg Ala Lys Ser Glu Gly Glu Gly Glu Val Ser Thr Pro Ser Thr Gln
65 70 75 80

```
Asp Asn Arg Ser Gly Glu Glu Ser Arg Val Ser Gly Arg Thr Ser Lys
                85                  90                  95

Pro Glu Ala Glu Ala His Ala Gly Asn Leu Asp Lys Gln Asn Ile His
            100                 105                 110

Arg Ala Phe Gly Gly Arg Thr Gly Thr Asn Ser Val Ser Gln Asp Leu
        115                 120                 125

Gly Asp Gly Gly Asp Ser Gly Ile Leu Glu Asn Pro Pro Asn Glu Arg
    130                 135                 140

Gly Tyr Pro Arg Ser Gly Ile Glu Asp Glu Asn Arg Glu Met Ala Ala
145                 150                 155                 160

His Pro Asp Lys Arg Gly Glu Asp Gln Ala Glu Gly Leu Pro Glu Glu
                165                 170                 175

Val Arg Gly Gly Thr Ser Leu Pro Asp Glu Gly Glu Gly Gly Ala Ser
            180                 185                 190

Asn Asn Gly Arg Ser Met Glu Pro Gly Ser Ser His Ser Ala Arg Val
        195                 200                 205

Thr Gly Val Leu Val Ile Pro Ser Pro Glu Leu Glu Glu Ala Val Leu
    210                 215                 220

Arg Arg Asn Lys Arg Arg Pro Thr Asn Ser Gly Ser Lys Pro Leu Thr
225                 230                 235                 240

Pro Ala Thr Val Pro Gly Thr Arg Ser Pro Pro Leu Asn Arg Tyr Asn
                245                 250                 255

Ser Thr Gly Ser Pro Pro Gly Lys Pro Pro Ser Thr Gln Asp Glu His
            260                 265                 270

Ile Asn Ser Gly Asp Thr Pro Ala Val Arg Val Lys Asp Arg Lys Pro
        275                 280                 285

Pro Ile Gly Thr Arg Ser Val Ser Asp Cys Pro Ala Asn Gly Arg Pro
    290                 295                 300

Ile His Pro Gly Leu Glu Thr Asp Ser Thr Lys Lys Gly Ile Gly Glu
305                 310                 315                 320

Asn Thr Ser Ser Met Lys Glu Met Ala Thr Leu Leu Thr Ser Leu Gly
                325                 330                 335

Val Ile Gln Ser Ala Gln Glu Phe Glu Ser Ser Arg Asp Ala Ser Tyr
            340                 345                 350

Val Phe Ala Arg Arg Ala Leu Lys Ser Ala Asn Tyr Ala Glu Met Thr
        355                 360                 365

Phe Asn Val Cys Gly Leu Ile Leu Ser Ala Glu Lys Ser Ser Ala Arg
    370                 375                 380

Lys Val Asp Glu Asn Lys Gln Leu Leu Lys Gln Ile Gln Glu Ser Val
385                 390                 395                 400

Glu Ser Phe Arg Asp Ile Tyr Lys Arg Phe Ser Glu Tyr Gln Lys Glu
                405                 410                 415

Gln Asn Ser Leu Leu Met Ser Asn Leu Ser Thr Leu His Ile Ile Thr
            420                 425                 430

Asp Arg Gly Gly Lys Thr Asp Asn Thr Asp Ser Leu Thr Arg Ser Pro
        435                 440                 445

Ser Val Phe Ala Lys Ser Lys Glu Asn Lys Thr Lys Ala Thr Arg Phe
    450                 455                 460

Asp Pro Ser Met Glu Thr Leu Glu Asp Met Lys Tyr Lys Pro Asp Leu
465                 470                 475                 480

Ile Arg Glu Asp Glu Phe Arg Asp Glu Ile Arg Asn Pro Leu Tyr Gln
                485                 490                 495
```

```
Glu Arg Asp Thr Glu Pro Arg Ala Ser Asn Ala Ser Arg Leu Leu Pro
            500                 505                 510

Ser Lys Glu Lys Pro Thr Met His Ser Leu Arg Leu Val Ile Glu Ser
        515                 520                 525

Ser Pro Leu Ser Arg Ala Glu Lys Ala Ala Tyr Val Lys Ser Leu Ser
    530                 535                 540

Lys Cys Lys Thr Asp Gln Glu Val Lys Ala Val Met Glu Leu Val Glu
545                 550                 555                 560

Glu Asp Ile Glu Ser Leu Thr Asn
                565


<210> SEQ ID NO 7
<211> LENGTH: 2228
<212> TYPE: PRT
<213> ORGANISM: Sendai virus

<400> SEQUENCE: 7

Met Asp Gly Gln Glu Ser Ser Gln Asn Pro Ser Asp Ile Leu Tyr Pro
1               5                   10                  15

Glu Cys His Leu Asn Ser Pro Ile Val Arg Gly Lys Ile Ala Gln Leu
            20                  25                  30

His Val Leu Leu Asp Val Asn Gln Pro Tyr Arg Leu Lys Asp Asp Ser
        35                  40                  45

Ile Ile Asn Ile Thr Lys His Lys Ile Arg Asn Gly Gly Leu Ser Pro
    50                  55                  60

Arg Gln Ile Lys Ile Arg Ser Leu Gly Lys Ala Leu Gln Arg Thr Ile
65                  70                  75                  80

Lys Asp Leu Asp Arg Tyr Thr Phe Asp Pro Tyr Pro Thr Tyr Ser Gln
                85                  90                  95

Glu Leu Leu Arg Leu Asp Ile Pro Glu Ile Cys Asp Lys Ile Arg Ser
            100                 105                 110

Val Phe Ala Val Ser Asp Arg Leu Thr Arg Glu Leu Ser Ser Gly Phe
        115                 120                 125

Gln Asp Leu Trp Leu Asn Ile Phe Lys Gln Leu Gly Asn Ile Glu Gly
    130                 135                 140

Arg Glu Gly Tyr Asp Pro Leu Gln Asp Ile Ser Thr Ile Pro Glu Ile
145                 150                 155                 160

Thr Asp Lys Tyr Ser Arg Asn Arg Trp Tyr Arg Pro Phe Leu Thr Trp
                165                 170                 175

Phe Ser Ile Lys Tyr Asp Met Arg Trp Met Gln Lys Thr Arg Pro Gly
            180                 185                 190

Gly Pro Leu Asp Thr Ser Asn Ser His Asn Leu Leu Glu Cys Lys Ser
        195                 200                 205

Tyr Thr Leu Val Thr Tyr Gly Asp Leu Val Met Ile Leu Asn Lys Leu
    210                 215                 220

Thr Leu Thr Gly Tyr Ile Leu Thr Pro Glu Leu Val Leu Met Tyr Cys
225                 230                 235                 240

Asp Val Val Glu Gly Arg Trp Asn Met Ser Ala Ala Gly His Leu Asp
                245                 250                 255

Lys Arg Ser Ile Gly Ile Thr Ser Lys Gly Glu Glu Leu Trp Glu Leu
            260                 265                 270

Val Asp Ser Leu Phe Ser Ser Leu Gly Glu Glu Ile Tyr Asn Val Ile
        275                 280                 285

Ala Leu Leu Glu Pro Leu Ser Leu Ala Leu Ile Gln Leu Asn Asp Pro
    290                 295                 300
```

-continued

```
Val Ile Pro Leu Arg Gly Ala Phe Met Arg His Val Leu Thr Glu Leu
305                 310                 315                 320

Gln Thr Val Leu Thr Ser Arg Asp Val Tyr Thr Asp Ala Glu Ala Asp
                325                 330                 335

Thr Ile Val Glu Ser Leu Leu Ala Ile Phe His Gly Thr Ser Ile Asp
            340                 345                 350

Glu Lys Ala Glu Ile Phe Ser Phe Phe Arg Thr Phe Gly His Pro Ser
        355                 360                 365

Leu Glu Ala Val Thr Ala Ala Asp Lys Val Arg Ala His Met Tyr Ala
    370                 375                 380

Gln Lys Ala Ile Lys Leu Lys Thr Leu Tyr Glu Cys His Ala Val Phe
385                 390                 395                 400

Cys Thr Ile Ile Ile Asn Gly Tyr Arg Glu Arg His Gly Gly Gln Trp
                405                 410                 415

Pro Pro Cys Asp Phe Pro Asp His Val Cys Leu Glu Leu Arg Asn Ala
            420                 425                 430

Gln Gly Ser Asn Thr Ala Ile Ser Tyr Glu Cys Ala Val Asp Asn Tyr
        435                 440                 445

Thr Ser Phe Ile Gly Phe Lys Phe Arg Lys Phe Ile Glu Pro Gln Leu
    450                 455                 460

Asp Glu Asp Leu Thr Ile Tyr Met Lys Asp Lys Ala Leu Ser Pro Arg
465                 470                 475                 480

Lys Glu Ala Trp Asp Ser Val Tyr Pro Asp Ser Asn Leu Tyr Tyr Lys
                485                 490                 495

Ala Pro Glu Ser Glu Glu Thr Arg Arg Leu Ile Glu Val Phe Ile Asn
            500                 505                 510

Asp Glu Asn Phe Asn Pro Glu Glu Ile Ile Asn Tyr Val Glu Ser Gly
        515                 520                 525

Asp Trp Leu Lys Asp Glu Lys Phe Asn Ile Ser Tyr Ser Leu Lys Glu
    530                 535                 540

Lys Glu Ile Lys Gln Glu Gly Arg Leu Phe Ala Lys Met Thr Tyr Lys
545                 550                 555                 560

Met Arg Ala Val Gln Val Leu Ala Glu Thr Leu Leu Ala Lys Gly Ile
                565                 570                 575

Gly Glu Leu Phe Ser Glu Asn Gly Met Val Lys Gly Glu Ile Asp Leu
            580                 585                 590

Leu Lys Arg Leu Thr Thr Leu Ser Val Ser Gly Val Pro Arg Thr Asp
        595                 600                 605

Ser Val Tyr Asn Asn Ser Lys Ser Ser Glu Lys Arg Asn Glu Gly Met
    610                 615                 620

Lys Lys Lys Asn Ser Gly Gly Tyr Trp Asp Glu Lys Lys Arg Ser Arg
625                 630                 635                 640

His Glu Phe Lys Ala Thr Asp Ser Ser Thr Asp Gly Tyr Glu Thr Leu
                645                 650                 655

Ser Cys Phe Leu Thr Thr Asp Leu Lys Lys Tyr Cys Leu Asn Trp Arg
            660                 665                 670

Phe Glu Ser Thr Ala Leu Phe Gly Gln Arg Cys Asn Glu Ile Phe Gly
        675                 680                 685

Phe Lys Thr Phe Phe Asn Trp Met His Pro Val Leu Glu Arg Cys Thr
    690                 695                 700

Ile Tyr Val Gly Asp Pro Tyr Cys Pro Val Ala Asp Arg Met His Arg
705                 710                 715                 720
```

-continued

```
Gln Leu Gln Asp His Ala Asp Ser Gly Ile Phe Ile His Asn Pro Arg
                725                 730                 735

Gly Gly Ile Glu Gly Tyr Cys Gln Lys Leu Trp Thr Leu Ile Ser Ile
            740                 745                 750

Ser Ala Ile His Leu Ala Ala Val Arg Val Gly Val Arg Val Ser Ala
        755                 760                 765

Met Val Gln Gly Asp Asn Gln Ala Ile Ala Val Thr Ser Arg Val Pro
    770                 775                 780

Val Ala Gln Thr Tyr Lys Gln Lys Lys Asn His Val Tyr Glu Glu Thr
785                 790                 795                 800

Thr Lys Tyr Phe Gly Ala Leu Arg His Val Met Phe Asp Val Gly His
                805                 810                 815

Glu Leu Lys Leu Asn Glu Thr Ile Ile Ser Ser Lys Met Phe Val Tyr
            820                 825                 830

Ser Lys Arg Ile Tyr Tyr Asp Gly Lys Ile Leu Pro Gln Cys Leu Lys
        835                 840                 845

Ala Leu Thr Arg Cys Val Phe Trp Ser Glu Thr Leu Val Asp Glu Asn
    850                 855                 860

Arg Ser Ala Cys Ser Asn Ile Ser Thr Ser Ile Ala Lys Ala Ile Glu
865                 870                 875                 880

Asn Gly Tyr Ser Pro Ile Leu Gly Tyr Cys Ile Ala Leu Tyr Lys Thr
                885                 890                 895

Cys Gln Gln Val Cys Ile Ser Leu Gly Met Thr Ile Asn Pro Thr Ile
            900                 905                 910

Ser Pro Thr Val Arg Asp Gln Tyr Phe Lys Gly Lys Asn Trp Leu Arg
        915                 920                 925

Cys Ala Val Leu Ile Pro Ala Asn Val Gly Gly Phe Asn Tyr Met Ser
    930                 935                 940

Thr Ser Arg Cys Phe Val Arg Asn Ile Gly Asp Pro Ala Val Ala Ala
945                 950                 955                 960

Leu Ala Asp Leu Lys Arg Phe Ile Arg Ala Asp Leu Leu Asp Lys Gln
                965                 970                 975

Val Leu Tyr Arg Val Met Asn Gln Glu Pro Gly Asp Ser Ser Phe Leu
            980                 985                 990

Asp Trp Ala Ser Asp Pro Tyr Ser  Cys Asn Leu Pro His  Ser Gln Ser
        995                 1000                1005

Ile Thr  Thr Ile Ile Lys Asn  Ile Thr Ala Arg Ser  Val Leu Gln
    1010                 1015                 1020

Glu Ser  Pro Asn Pro Leu Leu  Ser Gly Leu Phe Thr  Glu Thr Ser
    1025                 1030                 1035

Gly Glu  Glu Asp Leu Asn Leu  Ala Ser Phe Leu Met  Asp Arg Lys
    1040                 1045                 1050

Val Ile  Leu Pro Arg Val Ala  His Glu Ile Leu Gly  Asn Ser Leu
    1055                 1060                 1065

Thr Gly  Val Arg Glu Ala Ile  Ala Gly Met Leu Asp  Thr Thr Lys
    1070                 1075                 1080

Ser Leu  Val Arg Ala Ser Val  Arg Lys Gly Gly Leu  Ser Tyr Gly
    1085                 1090                 1095

Ile Leu  Arg Arg Leu Val Asn  Tyr Asp Leu Leu Gln  Tyr Glu Thr
    1100                 1105                 1110

Leu Thr  Arg Thr Leu Arg Lys  Pro Val Lys Asp Asn  Ile Glu Tyr
    1115                 1120                 1125
```

-continued

```
Glu Tyr  Met Cys Ser Val Glu  Leu Ala Val Gly Leu  Arg Gln Lys
    1130                 1135                 1140

Met Trp  Ile His Leu Thr Tyr  Gly Arg Pro Ile His  Gly Leu Glu
    1145                 1150                 1155

Thr Pro  Asp Pro Leu Glu Leu  Leu Arg Gly Thr Phe  Ile Glu Gly
    1160                 1165                 1170

Ser Glu  Val Cys Lys Leu Cys  Arg Ser Glu Gly Ala  Asp Pro Ile
    1175                 1180                 1185

Tyr Thr  Trp Phe Tyr Leu Pro  Asp Asn Ile Asp Leu  Asp Thr Leu
    1190                 1195                 1200

Thr Asn  Gly Ser Pro Ala Ile  Arg Ile Pro Tyr Phe  Gly Ser Ala
    1205                 1210                 1215

Thr Asp  Glu Arg Ser Glu Ala  Gln Leu Gly Tyr Val  Arg Asn Leu
    1220                 1225                 1230

Ser Lys  Pro Ala Lys Ala Ala  Ile Arg Ile Ala Met  Val Tyr Thr
    1235                 1240                 1245

Trp Ala  Tyr Gly Thr Asp Glu  Ile Ser Trp Met Glu  Ala Ala Leu
    1250                 1255                 1260

Ile Ala  Gln Thr Arg Ala Asn  Leu Ser Leu Glu Asn  Leu Lys Leu
    1265                 1270                 1275

Leu Thr  Pro Val Ser Thr Ser  Thr Asn Leu Ser His  Arg Leu Lys
    1280                 1285                 1290

Asp Thr  Ala Thr Gln Met Lys  Phe Ser Ser Ala Thr  Leu Val Arg
    1295                 1300                 1305

Ala Ser  Arg Phe Ile Thr Ile  Ser Asn Asp Asn Met  Ala Leu Lys
    1310                 1315                 1320

Glu Ala  Gly Glu Ser Lys Asp  Thr Asn Leu Val Tyr  Gln Gln Ile
    1325                 1330                 1335

Met Leu  Thr Gly Leu Ser Leu  Phe Glu Phe Asn Met  Arg Tyr Lys
    1340                 1345                 1350

Lys Gly  Ser Leu Gly Lys Pro  Leu Ile Leu His Leu  His Leu Asn
    1355                 1360                 1365

Asn Gly  Cys Cys Ile Met Glu  Ser Pro Gln Glu Ala  Asn Ile Pro
    1370                 1375                 1380

Pro Arg  Ser Thr Leu Asp Leu  Glu Ile Thr Gln Glu  Asn Asn Lys
    1385                 1390                 1395

Leu Ile  Tyr Asp Pro Asp Pro  Leu Lys Asp Val Asp  Leu Glu Leu
    1400                 1405                 1410

Phe Ser  Lys Val Arg Asp Val  Val His Thr Val Asp  Met Thr Tyr
    1415                 1420                 1425

Trp Ser  Asp Asp Glu Val Ile  Arg Ala Thr Ser Ile  Cys Thr Ala
    1430                 1435                 1440

Met Thr  Ile Ala Asp Thr Met  Ser Gln Leu Asp Arg  Asp Asn Leu
    1445                 1450                 1455

Lys Glu  Met Ile Ala Leu Val  Asn Asp Asp Asp Val  Asn Ser Leu
    1460                 1465                 1470

Ile Thr  Glu Phe Met Val Ile  Asp Val Pro Leu Phe  Cys Ser Thr
    1475                 1480                 1485

Phe Gly  Gly Ile Leu Val Asn  Gln Phe Ala Tyr Ser  Leu Tyr Gly
    1490                 1495                 1500

Leu Asn  Ile Arg Gly Arg Glu  Glu Ile Trp Gly His  Val Val Arg
    1505                 1510                 1515
```

-continued

```
Ile Leu  Lys Asp Thr Ser His  Ala Val Leu Lys Val  Leu Ser Asn
    1520                 1525                 1530

Ala Leu  Ser His Pro Lys Ile  Phe Lys Arg Phe Trp  Asn Ala Gly
    1535                 1540                 1545

Val Val  Glu Pro Val Tyr Gly  Pro Asn Leu Ser Asn  Gln Asp Lys
    1550                 1555                 1560

Ile Leu  Leu Ala Leu Ser Val  Cys Glu Tyr Ser Val  Asp Leu Phe
    1565                 1570                 1575

Met His  Asp Trp Gln Gly Gly  Val Pro Leu Glu Ile  Phe Ile Cys
    1580                 1585                 1590

Asp Asn  Asp Pro Asp Val Ala  Asp Met Arg Arg Ser  Ser Phe Leu
    1595                 1600                 1605

Ala Arg  His Leu Ala Tyr Leu  Cys Ser Leu Ala Glu  Ile Ser Arg
    1610                 1615                 1620

Asp Gly  Pro Arg Leu Glu Ser  Met Asn Ser Leu Glu  Arg Leu Glu
    1625                 1630                 1635

Ser Leu  Lys Ser Tyr Leu Glu  Leu Thr Phe Leu Asp  Asp Pro Val
    1640                 1645                 1650

Leu Arg  Tyr Ser Gln Leu Thr  Gly Leu Val Ile Lys  Val Phe Pro
    1655                 1660                 1665

Ser Thr  Leu Thr Tyr Ile Arg  Lys Ser Ser Ile Lys  Val Leu Arg
    1670                 1675                 1680

Thr Arg  Gly Ile Gly Val Pro  Glu Val Leu Glu Asp  Trp Asp Pro
    1685                 1690                 1695

Glu Ala  Asp Asn Ala Leu Leu  Asp Gly Ile Ala Ala  Glu Ile Gln
    1700                 1705                 1710

Gln Asn  Ile Pro Leu Gly His  Gln Thr Arg Ala Pro  Phe Trp Gly
    1715                 1720                 1725

Leu Arg  Val Ser Lys Ser Gln  Val Leu Arg Leu Arg  Gly Tyr Lys
    1730                 1735                 1740

Glu Ile  Thr Arg Gly Glu Ile  Gly Arg Ser Gly Val  Gly Leu Thr
    1745                 1750                 1755

Leu Pro  Phe Asp Gly Arg Tyr  Leu Ser His Gln Leu  Arg Leu Phe
    1760                 1765                 1770

Gly Ile  Asn Ser Thr Ser Cys  Leu Lys Ala Leu Glu  Leu Thr Tyr
    1775                 1780                 1785

Leu Leu  Ser Pro Leu Val Asp  Lys Asp Lys Asp Arg  Leu Tyr Leu
    1790                 1795                 1800

Gly Glu  Gly Ala Gly Ala Met  Leu Ser Cys Tyr Asp  Ala Thr Leu
    1805                 1810                 1815

Gly Pro  Cys Ile Asn Tyr Tyr  Asn Ser Gly Val Tyr  Ser Cys Asp
    1820                 1825                 1830

Val Asn  Gly Gln Arg Glu Leu  Asn Ile Tyr Pro Ala  Glu Val Ala
    1835                 1840                 1845

Leu Val  Gly Lys Lys Leu Asn  Asn Val Thr Ser Leu  Gly Gln Arg
    1850                 1855                 1860

Val Lys  Val Leu Phe Asn Gly  Asn Pro Gly Ser Thr  Trp Ile Gly
    1865                 1870                 1875

Asn Asp  Glu Cys Glu Ala Leu  Ile Trp Asn Glu Leu  Gln Asn Ser
    1880                 1885                 1890

Ser Ile  Gly Leu Val His Cys  Asp Met Glu Gly Gly  Asp His Lys
    1895                 1900                 1905
```

```
Asp Asp  Gln Val Val Leu His  Glu His Tyr Ser Val  Ile Arg Ile
    1910                 1915                 1920

Ala Tyr  Leu Val Gly Asp Arg  Asp Val Val Leu Ile  Ser Lys Ile
    1925                 1930                 1935

Ala Pro  Arg Leu Gly Thr Asp  Trp Thr Arg Gln Leu  Ser Leu Tyr
    1940                 1945                 1950

Leu Arg  Tyr Trp Asp Glu Val  Asn Leu Ile Val Leu  Lys Thr Ser
    1955                 1960                 1965

Asn Pro  Ala Ser Thr Glu Met  Tyr Leu Leu Ser Arg  His Pro Lys
    1970                 1975                 1980

Ser Asp  Ile Ile Glu Asp Ser  Lys Thr Val Leu Ala  Ser Leu Leu
    1985                 1990                 1995

Pro Leu  Ser Lys Glu Asp Ser  Ile Lys Ile Glu Lys  Trp Ile Leu
    2000                 2005                 2010

Ile Glu  Lys Ala Lys Ala His  Glu Trp Val Thr Arg  Glu Leu Arg
    2015                 2020                 2025

Glu Gly  Ser Ser Ser Ser Gly  Met Leu Arg Pro Tyr  His Gln Ala
    2030                 2035                 2040

Leu Gln  Thr Phe Gly Phe Glu  Pro Asn Leu Tyr Lys  Leu Ser Arg
    2045                 2050                 2055

Asp Phe  Leu Ser Thr Met Asn  Ile Ala Asp Thr His  Asn Cys Met
    2060                 2065                 2070

Ile Ala  Phe Asn Arg Val Leu  Gln Asp Thr Ile Phe  Glu Trp Ala
    2075                 2080                 2085

Arg Ile  Thr Glu Ser Asp Lys  Arg Leu Lys Leu Thr  Gly Lys Tyr
    2090                 2095                 2100

Asp Leu  Tyr Pro Val Arg Asp  Ser Gly Lys Leu Lys  Thr Ile Ser
    2105                 2110                 2115

Arg Arg  Leu Val Leu Ser Trp  Ile Ser Leu Ser Met  Ser Thr Arg
    2120                 2125                 2130

Leu Val  Thr Gly Ser Phe Pro  Asp Gln Lys Phe Glu  Ala Arg Leu
    2135                 2140                 2145

Gln Leu  Gly Ile Val Ser Leu  Ser Ser Arg Glu Ile  Arg Asn Leu
    2150                 2155                 2160

Arg Val  Ile Thr Lys Thr Leu  Leu Asp Arg Phe Glu  Asp Ile Ile
    2165                 2170                 2175

His Ser  Ile Thr Tyr Arg Phe  Leu Thr Lys Glu Ile  Lys Ile Leu
    2180                 2185                 2190

Met Lys  Ile Leu Gly Ala Val  Lys Met Phe Gly Ala  Ser Gln Asn
    2195                 2200                 2205

Glu Tyr  Thr Thr Val Ile Asp  Asp Gly Ser Leu Gly  Asp Ile Glu
    2210                 2215                 2220

Pro Tyr  Asp Ser Ser
    2225


<210> SEQ ID NO 8
<211> LENGTH: 348
<212> TYPE: PRT
<213> ORGANISM: Sendai virus

<400> SEQUENCE: 8

Met Ala Asp Ile Tyr Arg Phe Pro Lys Phe Ser Tyr Glu Asp Asn Gly
1               5                   10                  15

Thr Val Glu Pro Leu Pro Leu Arg Thr Gly Pro Asp Lys Lys Ala Ile
            20                  25                  30
```

-continued

```
Pro Tyr Ile Arg Ile Ile Lys Val Gly Asp Pro Pro Lys His Gly Val
        35                  40                  45

Arg Tyr Leu Asp Leu Leu Leu Leu Gly Phe Phe Glu Thr Pro Lys Gln
    50                  55                  60

Thr Thr Asn Leu Gly Ser Val Ser Asp Leu Thr Glu Pro Thr Ser Tyr
65                  70                  75                  80

Ser Ile Cys Gly Ser Gly Ser Leu Pro Ile Gly Val Ala Lys Tyr Tyr
                85                  90                  95

Gly Thr Asp Gln Glu Leu Leu Lys Ala Cys Thr Asp Leu Arg Ile Thr
            100                 105                 110

Val Arg Arg Thr Val Arg Ala Gly Glu Met Ile Val Tyr Met Val Asp
        115                 120                 125

Ser Ile Gly Ala Pro Leu Leu Pro Trp Ser Gly Arg Leu Arg Gln Gly
    130                 135                 140

Met Ile Phe Asn Ala Asn Lys Val Ala Leu Ala Pro Gln Cys Leu Pro
145                 150                 155                 160

Val Asp Lys Asp Ile Arg Phe Arg Val Val Phe Val Asn Gly Thr Ser
                165                 170                 175

Leu Gly Ala Ile Thr Ile Ala Lys Ile Pro Lys Thr Leu Ala Asp Leu
            180                 185                 190

Ala Leu Pro Asn Ser Ile Ser Val Asn Leu Leu Val Thr Leu Lys Thr
        195                 200                 205

Gly Ile Ser Thr Glu Gln Lys Gly Val Leu Pro Val Leu Asp Asp Gln
    210                 215                 220

Gly Glu Lys Lys Leu Asn Phe Met Val His Leu Gly Leu Ile Arg Arg
225                 230                 235                 240

Lys Val Gly Lys Ile Tyr Ser Val Glu Tyr Cys Lys Ser Lys Ile Glu
                245                 250                 255

Arg Met Arg Leu Ile Phe Ser Leu Gly Leu Ile Gly Gly Ile Ser Phe
            260                 265                 270

His Val Gln Val Thr Gly Thr Leu Ser Lys Thr Phe Met Ser Gln Leu
        275                 280                 285

Ala Trp Lys Arg Ala Val Cys Phe Pro Leu Met Asp Val Asn Pro His
    290                 295                 300

Met Asn Leu Val Ile Trp Ala Ala Ser Val Glu Ile Thr Gly Val Asp
305                 310                 315                 320

Ala Val Phe Gln Pro Ala Ile Pro Arg Asp Phe Arg Tyr Tyr Pro Asn
                325                 330                 335

Val Val Ala Lys Asn Ile Gly Arg Ile Arg Lys Leu
            340                 345
```

<210> SEQ ID NO 9
<211> LENGTH: 575
<212> TYPE: PRT
<213> ORGANISM: Sendai virus

<400> SEQUENCE: 9

```
Met Asp Gly Asp Arg Gly Lys Arg Asp Ser Tyr Trp Ser Thr Ser Pro
1               5                   10                  15

Ser Gly Ser Thr Thr Lys Leu Ala Ser Gly Trp Glu Arg Ser Ser Lys
            20                  25                  30

Val Asp Thr Trp Leu Leu Ile Leu Ser Phe Thr Gln Trp Ala Leu Ser
        35                  40                  45

Ile Ala Thr Val Ile Ile Cys Ile Ile Ile Ser Ala Arg Gln Gly Tyr
    50                  55                  60
```

-continued

```
Ser Met Lys Glu Tyr Ser Met Thr Val Glu Ala Leu Asn Met Ser Ser
65                  70                  75                  80

Arg Glu Val Lys Glu Ser Leu Thr Ser Leu Ile Arg Gln Glu Val Ile
                85                  90                  95

Ala Arg Ala Val Asn Ile Gln Ser Ser Val Gln Thr Gly Ile Pro Val
            100                 105                 110

Leu Leu Asn Lys Asn Ser Arg Asp Val Ile Gln Met Ile Asp Lys Ser
        115                 120                 125

Cys Ser Arg Gln Glu Leu Thr Gln Leu Cys Glu Ser Thr Ile Ala Val
    130                 135                 140

His His Ala Glu Gly Ile Ala Pro Leu Glu Pro His Ser Phe Trp Arg
145                 150                 155                 160

Cys Pro Val Gly Glu Pro Tyr Leu Ser Ser Asp Pro Lys Ile Ser Leu
                165                 170                 175

Leu Pro Gly Pro Ser Leu Leu Ser Gly Ser Thr Thr Ile Ser Gly Cys
            180                 185                 190

Val Arg Leu Pro Ser Leu Ser Ile Gly Glu Ala Ile Tyr Ala Tyr Ser
        195                 200                 205

Ser Asn Leu Ile Thr Gln Gly Cys Ala Asp Ile Gly Lys Ser Tyr Gln
    210                 215                 220

Val Leu Gln Leu Gly Tyr Ile Ser Leu Asn Ser Asp Met Phe Pro Asp
225                 230                 235                 240

Leu Asn Pro Val Val Ser His Thr Tyr Asp Ile Asn Asp Asn Arg Lys
                245                 250                 255

Ser Cys Ser Val Val Ala Thr Gly Thr Arg Gly Tyr Gln Leu Cys Ser
            260                 265                 270

Met Pro Thr Val Asp Glu Arg Thr Asp Tyr Ser Ser Asp Gly Ile Glu
        275                 280                 285

Asp Leu Val Leu Asp Val Leu Asp Leu Lys Gly Ser Thr Lys Ser His
    290                 295                 300

Arg Tyr Arg Asn Ser Glu Val Asp Leu Asp His Pro Phe Ser Ala Leu
305                 310                 315                 320

Tyr Pro Ser Val Gly Asn Gly Ile Ala Thr Glu Gly Ser Leu Ile Phe
                325                 330                 335

Leu Gly Tyr Gly Gly Leu Thr Thr Pro Leu Gln Gly Asp Thr Lys Cys
            340                 345                 350

Arg Thr Gln Gly Cys Gln Gln Val Ser Gln Asp Thr Cys Asn Glu Ala
        355                 360                 365

Leu Lys Ile Thr Trp Leu Gly Gly Lys Gln Val Val Ser Val Ile Ile
    370                 375                 380

Gln Val Asn Asp Tyr Leu Ser Glu Arg Pro Lys Ile Arg Val Thr Thr
385                 390                 395                 400

Ile Pro Ile Thr Gln Asn Tyr Leu Gly Ala Glu Gly Arg Leu Leu Lys
                405                 410                 415

Leu Gly Asp Arg Val Tyr Ile Tyr Thr Arg Ser Ser Gly Trp His Ser
            420                 425                 430

Gln Leu Gln Ile Gly Val Leu Asp Val Ser His Pro Leu Thr Ile Asn
        435                 440                 445

Trp Thr Pro His Glu Ala Leu Ser Arg Pro Gly Asn Glu Glu Cys Asn
    450                 455                 460

Trp Tyr Asn Thr Cys Pro Lys Glu Cys Ile Ser Gly Val Tyr Thr Asp
465                 470                 475                 480
```

```
Ala Tyr Pro Leu Ser Pro Asp Ala Ala Asn Val Ala Thr Val Thr Leu
                485                 490                 495

Tyr Ala Asn Thr Ser Arg Val Asn Pro Thr Ile Met Tyr Ser Asn Thr
            500                 505                 510

Thr Asn Ile Ile Asn Met Leu Arg Ile Lys Asp Val Gln Leu Glu Ala
        515                 520                 525

Ala Tyr Thr Thr Thr Ser Cys Ile Thr His Phe Gly Lys Gly Tyr Cys
    530                 535                 540

Phe His Ile Ile Glu Ile Asn Gln Lys Ser Leu Asn Thr Leu Gln Pro
545                 550                 555                 560

Met Leu Phe Lys Thr Ser Ile Pro Lys Leu Cys Lys Ala Glu Ser
                565                 570                 575


<210> SEQ ID NO 10
<211> LENGTH: 565
<212> TYPE: PRT
<213> ORGANISM: Sendai virus

<400> SEQUENCE: 10

Met Thr Ala Tyr Ile Gln Arg Ser Gln Cys Ile Ser Thr Ser Leu Leu
1               5                   10                  15

Val Val Leu Thr Thr Leu Val Ser Cys Gln Ile Pro Arg Asp Arg Leu
            20                  25                  30

Ser Asn Ile Gly Val Ile Val Asp Glu Gly Lys Ser Leu Lys Ile Ala
        35                  40                  45

Gly Ser His Glu Ser Arg Tyr Ile Val Leu Ser Leu Val Pro Gly Val
    50                  55                  60

Asp Leu Glu Asn Gly Cys Gly Thr Ala Gln Val Ile Gln Tyr Lys Ser
65                  70                  75                  80

Leu Leu Asn Arg Leu Leu Ile Pro Leu Arg Asp Ala Leu Asp Leu Gln
                85                  90                  95

Glu Ala Leu Ile Thr Val Thr Asn Asp Thr Thr Gln Asn Ala Gly Val
            100                 105                 110

Pro Gln Ser Arg Phe Phe Gly Ala Val Ile Gly Thr Ile Ala Leu Gly
        115                 120                 125

Val Ala Thr Ser Ala Gln Ile Thr Ala Gly Ile Ala Leu Ala Glu Ala
    130                 135                 140

Arg Glu Ala Lys Arg Asp Ile Ala Leu Ile Lys Glu Ser Met Thr Lys
145                 150                 155                 160

Thr His Lys Ser Ile Glu Leu Leu Gln Asn Ala Val Gly Glu Gln Ile
                165                 170                 175

Leu Ala Leu Lys Thr Leu Gln Asp Phe Val Asn Asp Glu Ile Lys Pro
            180                 185                 190

Ala Ile Ser Glu Leu Gly Cys Glu Thr Ala Ala Leu Arg Leu Gly Ile
        195                 200                 205

Lys Leu Thr Gln His Tyr Ser Gly Leu Leu Thr Ala Phe Gly Ser Asn
    210                 215                 220

Phe Gly Thr Ile Gly Glu Lys Ser Leu Thr Leu Gln Ala Leu Ser Ser
225                 230                 235                 240

Leu Tyr Ser Ala Asn Ile Thr Glu Ile Met Thr Thr Ile Arg Thr Gly
                245                 250                 255

Gln Ser Asn Ile Tyr Asp Val Ile Tyr Thr Glu Gln Ile Lys Gly Thr
            260                 265                 270
```

-continued

```
Val Ile Asp Val Asp Leu Glu Arg Tyr Met Val Thr Leu Ser Val Lys
        275                 280                 285

Ile Pro Ile Leu Ser Glu Val Pro Gly Val Leu Ile His Lys Ala Ser
    290                 295                 300

Ser Ile Ser Tyr Asn Ile Asp Gly Glu Glu Trp Tyr Val Thr Val Pro
305                 310                 315                 320

Ser His Ile Leu Ser Arg Ala Ser Phe Leu Gly Gly Ala Asp Ile Thr
                325                 330                 335

Asp Cys Val Glu Ser Arg Leu Thr Tyr Ile Cys Pro Arg Asp Pro Ala
            340                 345                 350

Gln Leu Ile Pro Asp Ser Gln Gln Lys Cys Ile Leu Gly Asp Thr Thr
        355                 360                 365

Arg Cys Pro Val Thr Lys Val Val Asp Ser Leu Ile Pro Lys Phe Ala
    370                 375                 380

Phe Val Asn Gly Gly Val Val Ala Asn Cys Ile Ala Ser Thr Cys Thr
385                 390                 395                 400

Cys Gly Thr Gly Arg Arg Pro Ile Ser Gln Asp Arg Ser Lys Gly Val
                405                 410                 415

Val Phe Leu Thr His Asp Asn Cys Gly Leu Ile Gly Val Asn Gly Val
            420                 425                 430

Glu Leu Tyr Ala Asn Arg Arg Gly His Asp Ala Thr Trp Gly Val Gln
        435                 440                 445

Asn Leu Thr Val Gly Pro Ala Ile Ala Ile Arg Pro Ile Asp Ile Ser
    450                 455                 460

Leu Asn Leu Ala Asp Ala Thr Asn Phe Leu Gln Asp Ser Lys Ala Glu
465                 470                 475                 480

Leu Glu Lys Ala Arg Lys Ile Leu Ser Glu Val Gly Arg Trp Tyr Asn
                485                 490                 495

Ser Arg Glu Thr Val Ile Thr Ile Ile Val Val Met Val Val Ile Leu
            500                 505                 510

Val Val Ile Ile Val Ile Val Ile Val Leu Tyr Arg Leu Lys Arg Ser
        515                 520                 525

Met Leu Met Gly Asn Pro Asp Asp Arg Ile Pro Arg Asp Thr Tyr Thr
    530                 535                 540

Leu Glu Pro Lys Ile Arg His Met Tyr Thr Asn Gly Gly Phe Asp Ala
545                 550                 555                 560

Met Ala Glu Lys Arg
                565


<210> SEQ ID NO 11
<211> LENGTH: 11
<212> TYPE: PRT
<213> ORGANISM: Human immunodeficiency virus

<400> SEQUENCE: 11

Tyr Gly Arg Lys Lys Arg Arg Gln Arg Arg Arg
1               5                   10


<210> SEQ ID NO 12
<211> LENGTH: 9
<212> TYPE: PRT
<213> ORGANISM: Human immunodeficiency virus

<400> SEQUENCE: 12

Arg Lys Lys Arg Arg Gln Arg Arg Arg
1               5
```

-continued

<210> SEQ ID NO 13
<211> LENGTH: 7
<212> TYPE: PRT
<213> ORGANISM: Artificial Sequence
<220> FEATURE:
<223> OTHER INFORMATION: Synthetic polyarginine

<400> SEQUENCE: 13

```
Arg Arg Arg Arg Arg Arg Arg
1               5
```

<210> SEQ ID NO 14
<211> LENGTH: 12
<212> TYPE: PRT
<213> ORGANISM: Unknown
<220> FEATURE:
<223> OTHER INFORMATION: Protein transduction domain

<400> SEQUENCE: 14

```
Arg Arg Gln Arg Arg Thr Ser Lys Leu Met Lys Arg
1               5                   10
```

<210> SEQ ID NO 15
<211> LENGTH: 27
<212> TYPE: PRT
<213> ORGANISM: Unknown
<220> FEATURE:
<223> OTHER INFORMATION: Transportan

<400> SEQUENCE: 15

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 16
<211> LENGTH: 33
<212> TYPE: PRT
<213> ORGANISM: Unknown
<220> FEATURE:
<223> OTHER INFORMATION: Protein transduction domain

<400> SEQUENCE: 16

```
Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

<210> SEQ ID NO 17
<211> LENGTH: 16
<212> TYPE: PRT
<213> ORGANISM: Unknown
<220> FEATURE:
<223> OTHER INFORMATION: Protein transduction domain

<400> SEQUENCE: 17

```
Arg Gln Ile Lys Ile Trp Phe Gln Asn Arg Arg Met Lys Trp Lys Lys
1               5                   10                  15
```

<210> SEQ ID NO 18
<211> LENGTH: 1329
<212> TYPE: DNA
<213> ORGANISM: Artificial Sequence
<220> FEATURE:
<223> OTHER INFORMATION: Synthetic PCR-produced DNA template

<400> SEQUENCE: 18
taatacgact cactatagga ccaaacaaga gaaaaaacat gtatggaata tataatgaag 60
tcagacagga ttttagggtc aaagtatcca ccctgaggag caggttccag accctttgct 120
ttgctgccaa agttcacgat gcccgccatg aagatcgagt gccgcatcac cggcaccctg 180
aacggcgtgg agttcgagct ggtgggcggc ggagagggca cccccgagca gggccgcatg 240
accaacaaga tgaagagcac caagggcgcc ctgaccttca gcccctacct gctgagccac 300
gtgatgggct acggcttcta ccacttcggc acctacccca gcggctacga gaaccccttc 360
ctgcacgcca tcaacaacgg cggctacacc aacacccgca tcgagaagta cgaggacggc 420
ggcgtgctgc acgtgagctt cagctaccgc tacgaggccg gccgcgtgat cggcgacttc 480
aaggtggtgg gcaccggctt ccccgaggac agcgtgatct tcaccgacaa gatcatccgc 540
agcaacgcca ccgtggagca cctgcacccc atgggcgata acgtgctggt gggcagcttc 600
gcccgcacct tcagcctgcg cgacggcggc tactacagct tcgtggtgga cagccacatg 660
cacttcaaga gcgccatcca ccccagcatc ctgcagaacg gggggcccat gttcgccttc 720
cgccgcgtgg aggagctgca cagcaacacc gagctgggca tcgtggagta ccagcacgcc 780
ttcaagaccc cgatcgcatt cgccagatct cgagctcgat aataattagt ccctatcgtg 840
cagaacgatc gaagctccgc ggtacctgga agtcttggac ttatccatat gacaatagta 900
agaaaaactt acaagaagac aagaaaattt aaaagaataa atatctctta aactcttgtc 960
tggtggccgg catggtccca gcctcctcgc tggcgccggc tgggcaacat tccgagggga 1020
ccgtcccctc ggtaatggcg aatgggacgg atccctgcag ctcgagaggc ctaattaatt 1080
aagtcgacga tccggctgct aacaaagccc gaaaggaagc tgagttggct gctgccaccg 1140
ctgagcaata actagcataa ccccttgggg cctctaaacg ggtcttgagg ggttttttgc 1200
tgaaaggagg aactatatcc ggatcgagaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaa 1329

<210> SEQ ID NO 19
<211> LENGTH: 1302
<212> TYPE: DNA
<213> ORGANISM: Artificial Sequence
<220> FEATURE:
<223> OTHER INFORMATION: Synthetic DNA template

<400> SEQUENCE: 19
taatacgact cactatagga ccagacaaga gtttaagaga tatttattct tttaaatttt 60
cttgtcttct tgtaagtttt tcttactatt gtcatatgga taagtccaag acttccaggt 120
accgcggagc ttcgatcgtt ctgcacgata gggactaacc attattatcg agctcgagat 180
ctggcgaatg cgatcggggt cttgaaggcg tgctggtact ccacgatgcc cagctcggtg 240
ttgctgtgca gctcctccac gcggcggaag gcgaacatgg ggcccccgtt ctgcaggatg 300
ctggggtgga tggcgctctt gaagtgcatg tggctgtcca ccacgaagct gtagtagccg 360
ccgtcgcgca ggctgaaggt gcgggcgaag ctgcccacca gcacgttatc gcccatgggg 420
tgcaggtgct ccacggtggc gttgctgcgg atgatcttgt cggtgaagat cacgctgtcc 480
tcggggaagc cggtgcccac caccttgaag tcgccgatca cgcggccggc ctcgtagcgg 540
tagctgaagc tcacgtgcag cacgccgccg tcctcgtact tctcgatgcg ggtgttggtg 600
tagccgccgt tgttgatggc gtgcaggaag ggttctcgt agccgctggg gtaggtgccg 660

```
aagtggtaga agccgtagcc catcacgtgg ctcagcaggt aggggctgaa ggtcagggcg    720

cccttggtgc tcttcatctt gttggtcatg cggccctgct cgggggtgcc ctctccgccg    780

cccaccagct cgaactccac gccgttcagg gtgccggtga tgcggcactc gatcttcatg    840

gcgggcatcg tgaactttgg cagcaaagca aagggtctgg aacctgctcc tcagggtgga    900

tactttgacc ctaaaatcct gtctgacttc attatatatt ccatacatgt tttttctctt    960

gtttggtggc cggcatggtc ccagcctcct cgctggcgcc ggctgggcaa cattccgagg   1020

ggaccgtccc ctcggtaatg gcgaatggga cggatccctg cagctcgaga ggcctaatta   1080

attaagtcga cgatccggct gctaacaaag cccgaaagga agctgagttg gctgctgcca   1140

ccgctgagca ataactagca taaccccttg gggcctctaa acgggtcttg aggggttttt   1200

tgaaaaaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aa                      1302


<210> SEQ ID NO 20
<211> LENGTH: 2024
<212> TYPE: DNA
<213> ORGANISM: Artificial Sequence
<220> FEATURE:
<223> OTHER INFORMATION: Synthetic DNA template

<400> SEQUENCE: 20

taatacgact cactatagga ccagacaaga gtttaagaga tatttattct tttaaatttt     60

cttgtcttct tgtaagtttt tcttactatt gtcatatgga taagtccaag acttccaggt    120

accgcggagc ttcgatcgtt ctgcacgata gggactaacc attattagaa gaactcgtca    180

agaaggcgat agaaggcgat gcgctgcgaa tcgggagcgg cgataccgta aagcacgagg    240

aagcggtcag cccattcgcc gccaagctct tcagcaatat cacgggtagc caacgctatg    300

tcctgatagc ggtccgccac acccagccgg ccacagtcga tgaatccaga aaagcggcca    360

ttttccacca tgatattcgg caagcaggca tcgccatggg tcacgacgag atcctcgccg    420

tcgggcatgc gcgccttgag cctggcgaac agttcggctg gcgcgagccc ctgatgctct    480

tcgtccagat catcctgatc gacaagaccg gcttccatcc gagtacgtgc tcgctcgatg    540

cgatgtttcg cttggtggtc gaatgggcag gtagccggat caagcgtatg cagccgccgc    600

attgcatcag ccatgatgga tactttctcg gcaggagcaa ggtgagatga caggagatcc    660

tgccccggca cttcgcccaa tagcagccag tcccttcccg cttcagtgac aacgtcgagc    720

acagctgcgc aaggaacgcc cgtcgtggcc agccacgata gccgcgctgc ctcgtcctgc    780

agttcattca gggcaccgga caggtcggtc ttgacaaaaa gaaccgggcg cccctgcgct    840

gacagccgga acacggcggc atcagagcag ccgattgtct gttgtgccca gtcatagccg    900

aatagcctct ccacccaagc ggccggagaa cctgcgtgca atccatcttg ttcaataacc    960

atggttgtgg cgtgatggtg atggtgatgt cgagctcgag atctggcgaa tgcgatcggg   1020

gtcttgaagg cgtgctggta ctccacgatg cccagctcgg tgttgctgtg cagctcctcc   1080

acgcggcgga aggcgaacat ggggcccccg ttctgcagga tgctggggtg gatggcgctc   1140

ttgaagtgca tgtggctgtc caccacgaag ctgtagtagc cgccgtcgcg caggctgaag   1200

gtgcgggcga agctgcccac cagcacgtta tcgcccatgg ggtgcaggtg ctccacggtg   1260

gcgttgctgc ggatgatctt gtcggtgaag atcacgctgt cctcggggaa gccggtgccc   1320

accaccttga agtcgccgat cacgcggccg gcctcgtagc ggtagctgaa gctcacgtgc   1380

agcacgccgc cgtcctcgta cttctcgatg cgggtgttgg tgtagccgcc gttgttgatg   1440
```

-continued

```
gcgtgcagga aggggttctc gtagccgctg ggtaggtgc  cgaagtggta gaagccgtag   1500
cccatcacgt ggctcagcag gtaggggctg aaggtcaggg cgcccttggt gctcttcatc   1560
ttgttggtca tgcggccctg ctcgggggtg ccctctccgc cgcccaccag ctcgaactcc   1620
acgccgttca gggtgccggt gatgcggcac tcgatcttca tggcgggcat cgtgaacttt   1680
ggcagcaaag caaagggtct ggaacctgct cctcagggtg gatactttga ccctaaaatc   1740
ctgtctgact tcattatata ttccatacat gttttttctc ttgtttggtg gccggcatgg   1800
tcccagcctc ctcgctggcg ccggctgggc aacattccga ggggaccgtc ccctcggtaa   1860
tggcgaatgg gacggatccc tgcagctcga gaggcctaat taattaagtc gacgatccgg   1920
ctgctaacaa agcccgaaag gaagctgagt tggctgctgc caccgctgag caataactag   1980
cataacccct tggggcctct aaacgggtct tgaggggttt tttg                    2024
```